(12) United States Patent
Torikai et al.

(10) Patent No.: US 12,290,560 B2
(45) Date of Patent: May 6, 2025

(54) VACCINE FOR PREVENTING OR TREATING CONGENITAL INFECTION WITH CYTOMEGALOVIRUS

(71) Applicant: KM Biologics Co., Ltd., Kumamoto (JP)

(72) Inventors: Masaharu Torikai, Kumamoto (JP); Hiroaki Mori, Kumamoto (JP); Tomohiro Nishimura, Kumamoto (JP); Takahiro Katayama, Kanagawa (JP); Kohsuke Hazeyama, Kumamoto (JP); Miyuki Matsumoto, Kumamoto (JP); Hiroyuki Shimizu, Saitama (JP); Naoki Inoue, Gifu (JP)

(73) Assignee: KM Biologics Co., Ltd., Kumamoto (JP)

( * ) Notice: Subject to any disclaimer, the term of this patent is extended or adjusted under 35 U.S.C. 154(b) by 71 days.

(21) Appl. No.: 17/312,235

(22) PCT Filed: Dec. 6, 2019

(86) PCT No.: PCT/JP2019/047966
§ 371 (c)(1),
(2) Date: Jun. 9, 2021

(87) PCT Pub. No.: WO2020/121983
PCT Pub. Date: Jun. 18, 2020

(65) Prior Publication Data
US 2022/0023416 A1    Jan. 27, 2022

(30) Foreign Application Priority Data
Dec. 10, 2018 (JP) .................. 2018-230640

(51) Int. Cl.
A61K 39/245 (2006.01)
A61P 31/20 (2006.01)
(Continued)

(52) U.S. Cl.
CPC ............ *A61K 39/245* (2013.01); *A61P 31/20* (2018.01); *C12N 7/00* (2013.01); *A61K 2039/552* (2013.01)

(58) Field of Classification Search
None
See application file for complete search history.

(56) References Cited

U.S. PATENT DOCUMENTS

| | | |
|---|---|---|
| 10,064,935 B2 | 9/2018 | Ciaramella et al. |
| 10,111,945 B2 | 10/2018 | Orlinger et al. |

(Continued)

FOREIGN PATENT DOCUMENTS

| | | |
|---|---|---|
| CA | 3075207 A1 | 3/2019 |
| CA | 3078207 A1 | 10/2021 |

(Continued)

OTHER PUBLICATIONS

Sequence alignment of alignment instant of SEQ ID No. 1 with Geneseq database accession No. BKL33489—2022.*

(Continued)

*Primary Examiner* — Shanon A. Foley
(74) *Attorney, Agent, or Firm* — Pillsbury Winthrop Shaw

(57) ABSTRACT

An object of the present invention is to provide an effective vaccine capable of preventing and treating congenital infection with CMV. The vaccine for preventing or treating congenital infection with cytomegalovirus (CMV) according to the present invention comprises a CMV envelope glycoprotein B (gB protein) antigen and a pentamer antigen.

4 Claims, 13 Drawing Sheets

Specification includes a Sequence Listing.

(51) Int. Cl.
    *C12N 7/00*     (2006.01)
    *A61K 39/00*    (2006.01)

(56) References Cited

U.S. PATENT DOCUMENTS

| | | | |
|---|---|---|---|
| 2005/0164365 A1 | 7/2005 | Yonemura et al. | |
| 2022/0023416 A1* | 1/2022 | Torikai | C07K 14/005 |

FOREIGN PATENT DOCUMENTS

| | | | |
|---|---|---|---|
| CN | 105980570 A | | 9/2016 |
| CN | 106460010 A | | 2/2017 |
| CN | 107075486 A | | 8/2017 |
| EP | 3015475 A1 | | 5/2016 |
| JP | 2017-503482 A | | 2/2017 |
| JP | 2017-515503 A | | 6/2017 |
| WO | 2003/004647 A1 | | 1/2003 |
| WO | WO2012/049317 | * | 4/2012 |
| WO | 2014/005959 A1 | | 1/2014 |
| WO | 2015/082570 A1 | | 6/2015 |
| WO | 2015/170287 A1 | | 11/2015 |
| WO | 2017/153954 A1 | | 9/2017 |
| WO | WO 2019/052975 | * | 3/2019 |

OTHER PUBLICATIONS

Sun et al. (Journal of Bioscience. 2007; 32 (6): 1111-1118).*
Sequence alignment of instant SEQ 2 with Geneseq database accession No. BFT47284—2018.*
Sequence alignment of instant SEQ 3 with Geneseq database access No. BAJ75101—2013.*
Sequence alignment of instant SEQ 4 with Geneseq database accession No. BFT47294—2018.*
Sequence alignment of instant SEQ 5 with Geneseq database accession No. BBB52383—2014.*
Sequence alignment of instant SEQ 6 with Geneseq database accession No. ADP81637—2007.*
Shepp et al. (Research in virology 149.2 (1998): 109-114).*
Yamaguchi et al. (Vaccine. 2023; 41: 4497-4507).*
Seq alignment of aa residue substituted SEQ ID 7 with Geneseq db access No. AZV29657 in WO2012/049317, Apr. 2012.*
Patent Cooperation Treaty, International Preliminary Report on Patentability issued in PCT/JP2019/047966, Jun. 24, 2021, pp. 1-7.
European Patent Office, European Search Report issued in EP 19896311.8, Sep. 21, 2022, pp. 1-9.
McVoy et al., "A Cytomegalovirus DNA Vaccine Induces Antibodies that Block Viral Entry into Fibroblasts and Epithelial Cells", Vaccine, Dec. 16, 2015, pp. 7328-7336, vol. 33(51).
Patent Cooperation Treaty, International Search Report issued in PCT/JP2019/047966, Oct. 2, 2020, pp. 1-2.
Azuma et al., "Cytomegalovirus seropositivity in pregnant women in Japan during 1996-2009", J Jpn Soc Perin Neon Med, 2010, pp. 1273-1279, vol. 46.

Stratton et al., "Vaccines for the 21st century: a Tool for Decisionmaking", The National Academies Press, 2000, pp. 1-473.
Revello, M.D et al., "A Randomized Trial of Hyperimmune Globulin to Prevent Congenital Cytomegalovirus", The New England Journal of Medicine, 2014, pp. 1316-1326, vol. 370.
Rieder et al., "Cytomegalovirus vaccine: phase II clinical trial results", Clin Microbiol Infect, 2014, pp. 95-102, vol. 20 Suppl 5.
Yamada et al., "Characterization of the guinea pig cytomegalovirus genome locus that encodes homologs of human cytomegalovirus major immediate-early genes, UL128, and UL130", Virology, 2009, pp. 99-106, vol. 391.
Schleiss et al., "Glycoprotein B(GB) vaccines adjuvanted with AS01 or AS02 protect female guinea pigs against cytomegalovirus (CMV) viremia and offspring mortality in a CMV-challenge model", Vaccine, 2014, pp. 2756-2762, vol. 32.
Hashimoto et al., "Effects of immunization of pregnant guinea pigs with guinea pig cytomegalovirus glycoprotein B on viral spread in the placenta", Vaccine, 2013, pp. 3199-3205, vol. 31.
Coleman et al., "A Homolog Pentameric Complex Dictates Viral Epithelial Tropism, Pathogenicity and Congenital Infection Rate in Guinea Pig Cytomegalovirus", PLOS Pathogens, 2016, pp. 1-38, vol. 12.
Zydek et al., "HCMV Infection of Human Trophoblast Progenitor Cells of the Placenta is Neutralized by a Human Monoclonal Antibody to Glycoprotein B and Not by Antibodies to the Pentamer Complex", Viruses, 2014, pp. 1346-1364. vol. 6.
Yamada et al., "An Ex vivo culture model for placental cytomegalovirus infection using slices of Guinea pig placental issue", Placenta, 2016, pp. 85-88, vol. 37.
Patel et al., "In Vitro Characterization of Human Cytomegalovirus-Targeting Therapeutic Monoclonal Antibodies JP538 and LJP539", Antimicrob Agents Chemother, 2016, pp. 4961-4971, vol. 60.
Burke et al., "Crystal Structure of the Human Cytomegalovirus Glycoprotein B", PLoS Pathog, 2015, pp. 1-21, vol. 11, e1005227.
Ciferri et al., "Structural and biochemical studies of HCMV gH/gL/gO and Pentamer reveal mutually exclusive cell entry complexes", Proc Natl Acad Sci USA, 2015, pp. 1767-1772, vol. 112.
Kanai et al., "Re-evaluation of the genome sequence of guinea pig cytomegalovirus", J Gen Virol, 2011, pp. 1005-1020, vol. 92(Pt 5).
Yamada et al., "Guinea pig cytomegalovirus GP129/131/133, homologues of human cytomegalovirus UL 128/130/131A, are necessary for infection of monocytes and macrophages", J Gen Virol, 2014, pp. 1376-1382, vol. 95(Pt 6).
Chiuppesi, et al., "Vaccine-Derived Neutralizing Antibodies to the Human Cytomegalovirus gH/gL Pentamer Potently Block Primary Cytotrophoblast Infection", Journal of Virology, 2015, pp. 11884-11898, vol. 89(23).
National Center for Biotechnology Information, "Human cytomegalovirus strain AD169 complete genome", NCBI, Jul. 26, 2016, GenBank Accession No. X17403.1.
National Center for Biotechnology Information, "Human herpesvirus 5 strain Merlin, complete genome", NCBI, Jul. 2, 2013, GenBank Accession No. AY446894.2.
Canadian Intellectual Property Office, Official Action issued in CA 3,121,915, Jul. 31, 2023, pp. 1-6.

* cited by examiner

Fig.9
(A)
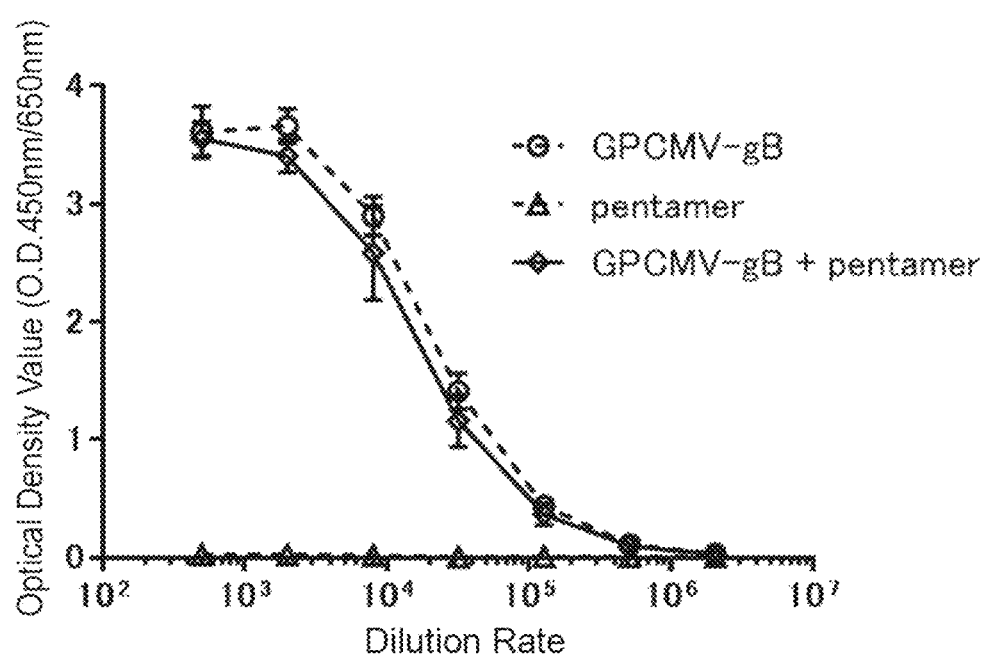
(B)
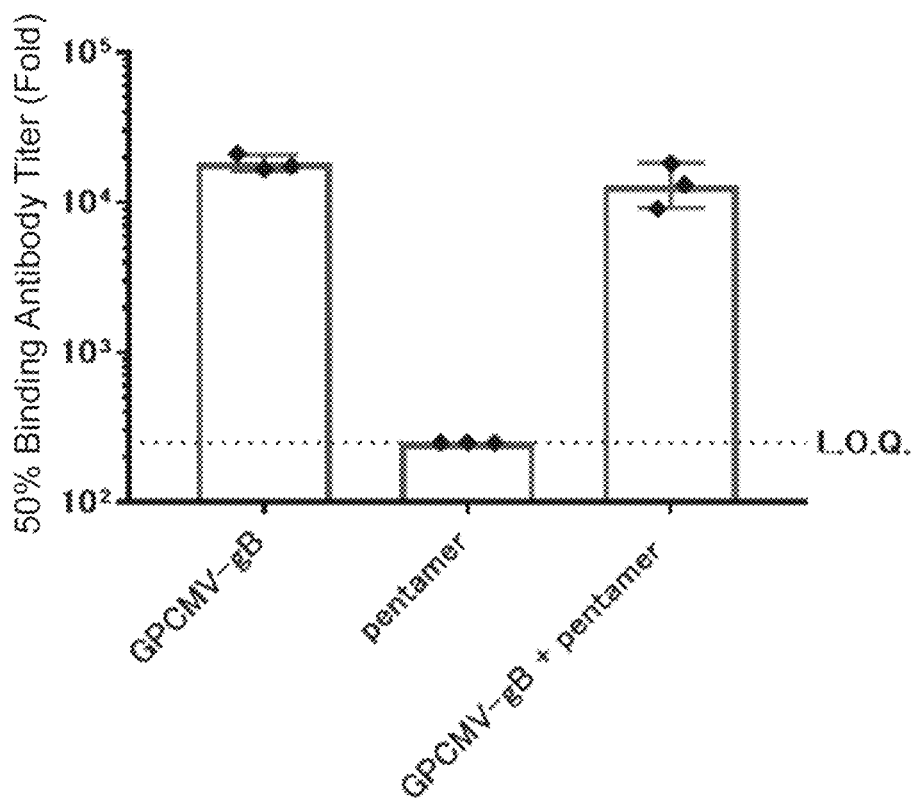

Fig. 10
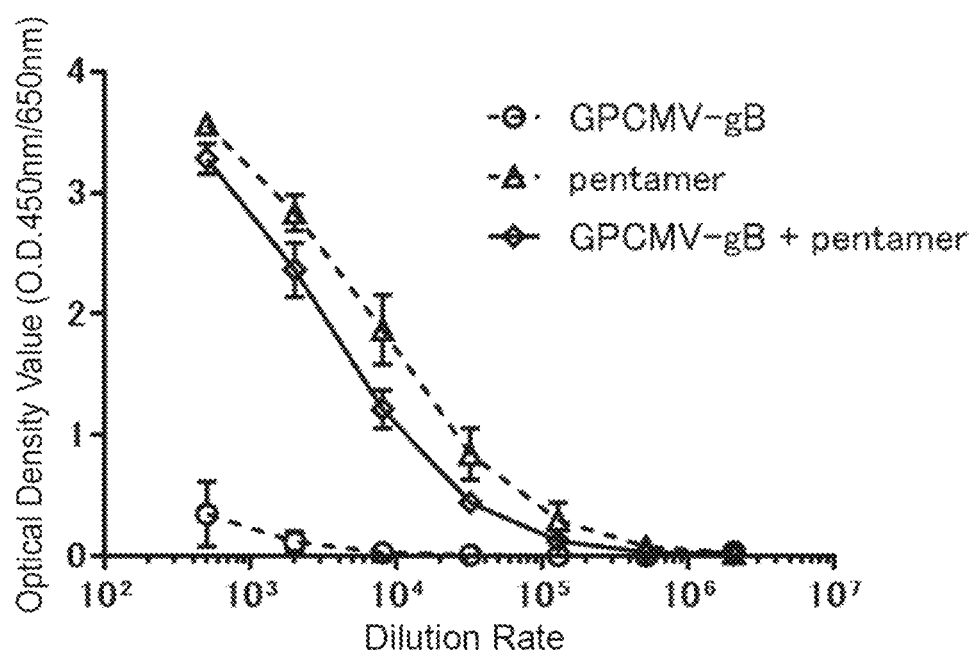
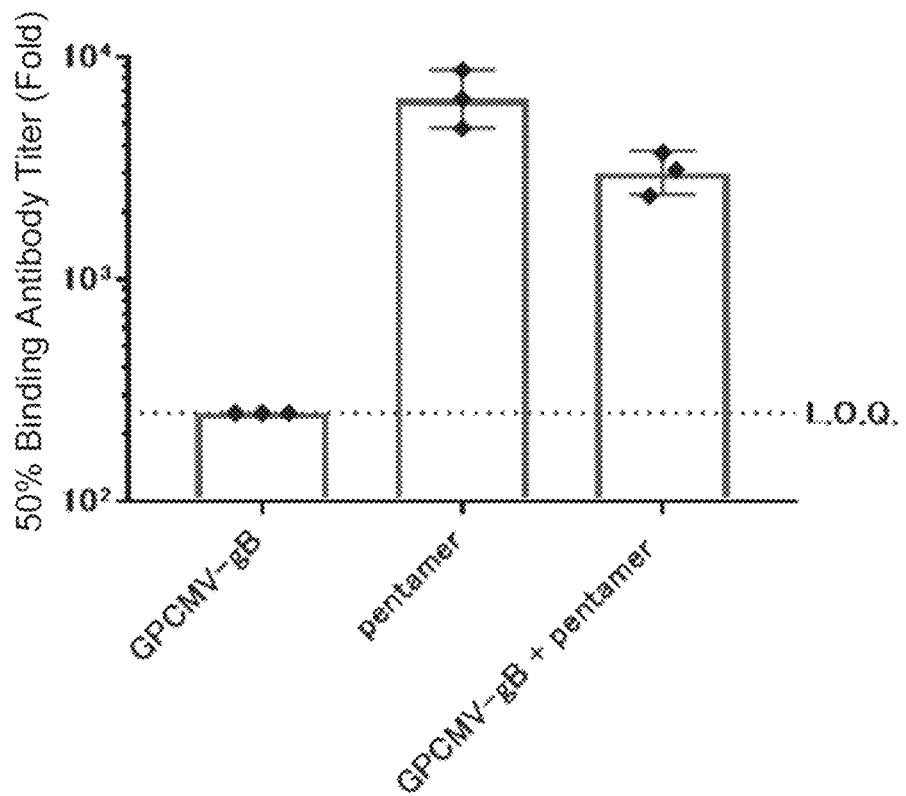

Fig.11
(A)
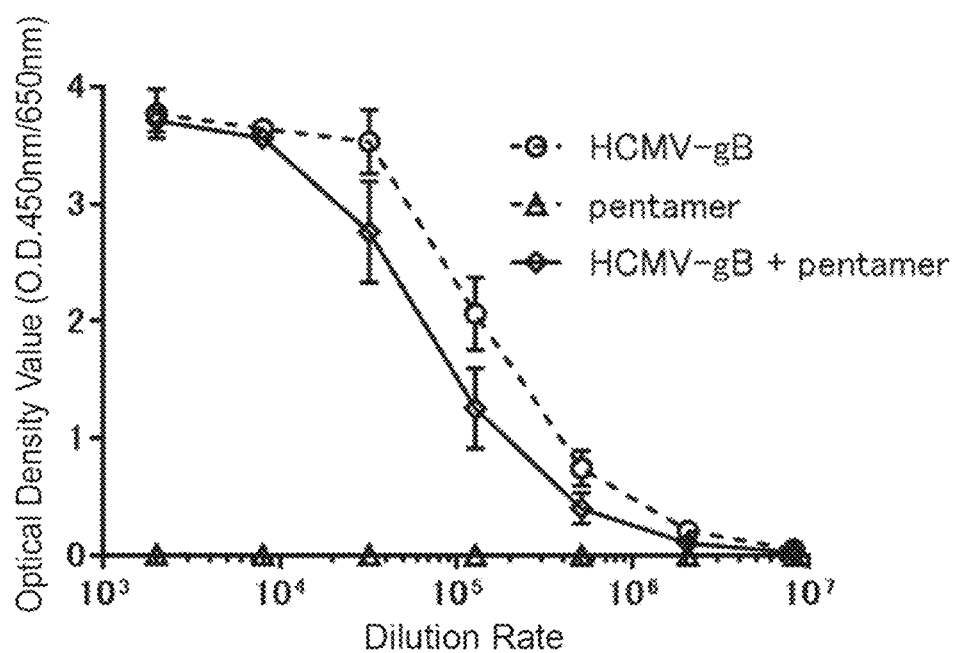
(B)
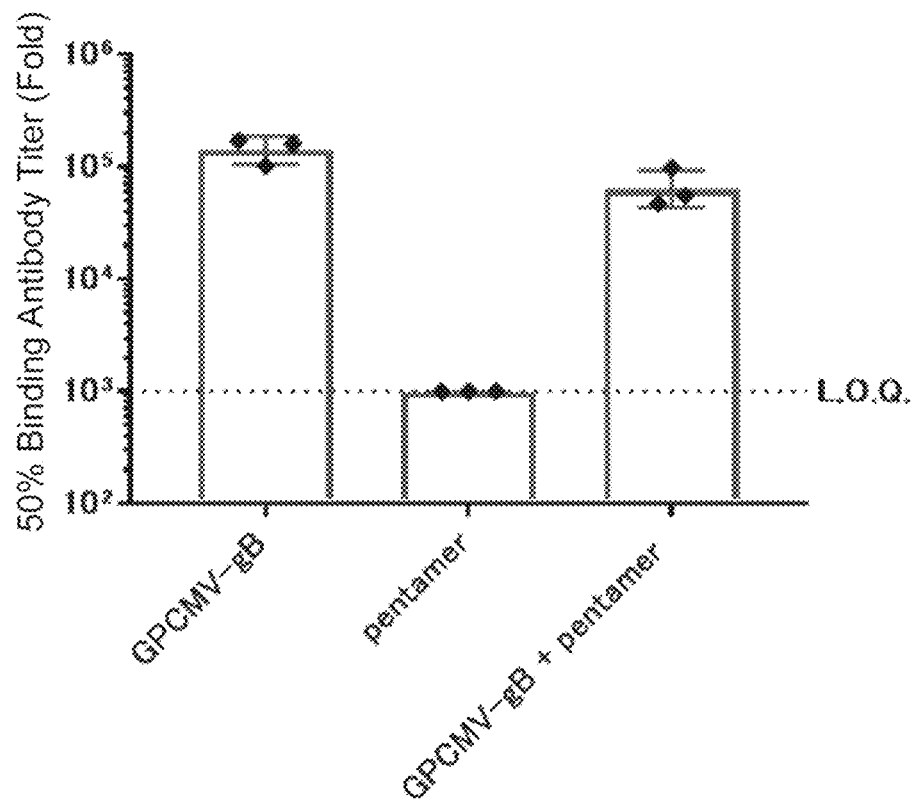

Fig. 12
(A)
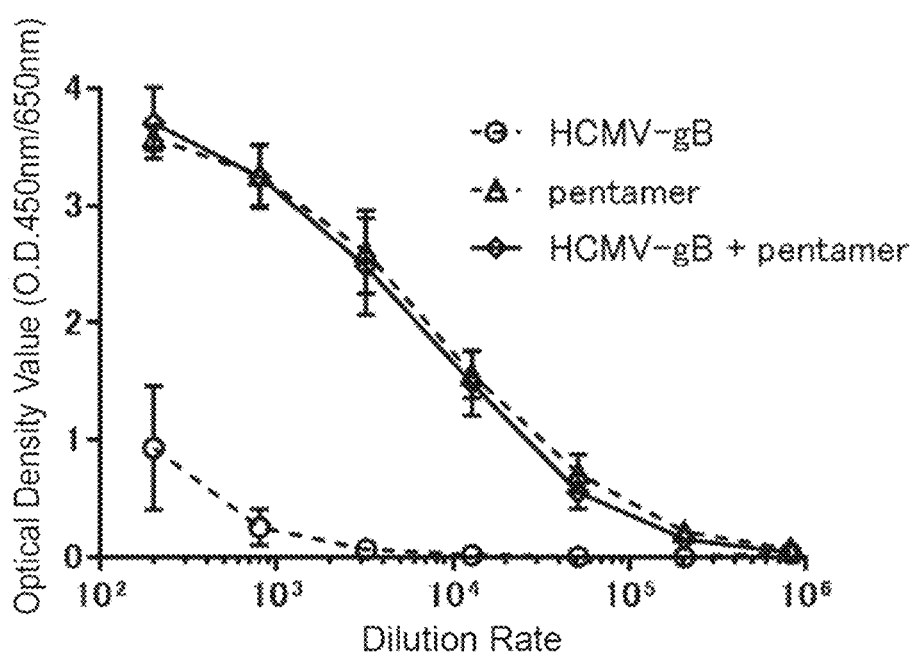
(B)
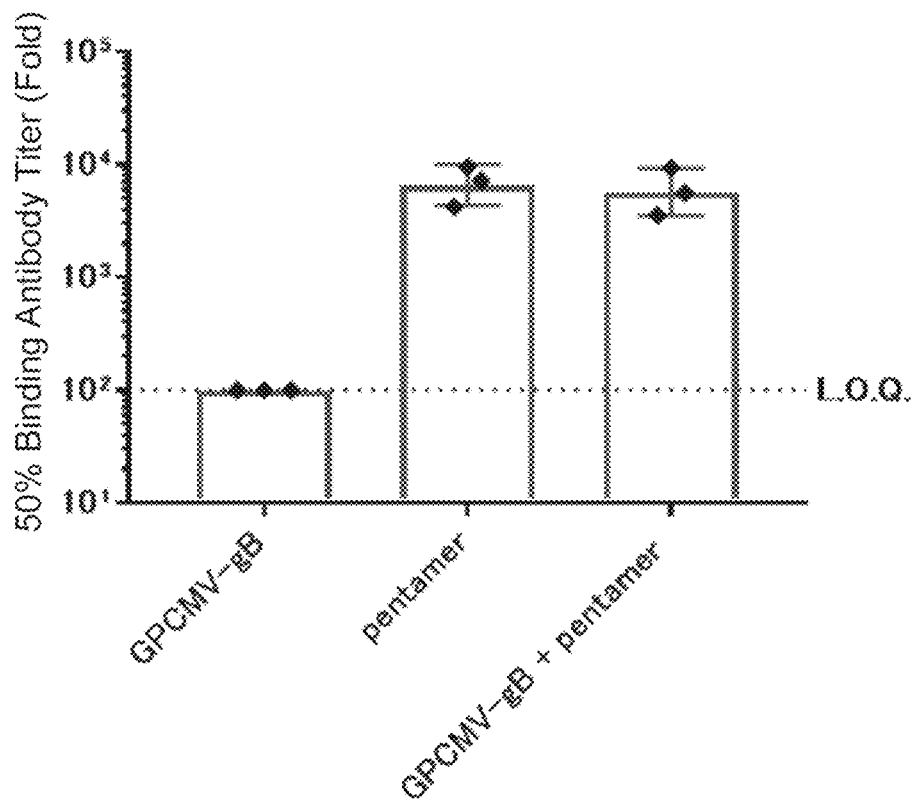

SEQUENCE LISTING

```
<160> NUMBER OF SEQ ID NOS: 22

<210> SEQ ID NO 1
<211> LENGTH: 706
<212> TYPE: PRT
<213> ORGANISM: Human cytomegalovirus
<220> FEATURE:
<223> OTHER INFORMATION: gB1-682-fm3Mv9

<400> SEQUENCE: 1

Met Glu Ser Arg Ile Trp Cys Leu Val Val Cys Val Asn Leu Cys Ile
1               5                   10                  15

Val Cys Leu Gly Ala Ala Val Ser Ser Ser Thr Ser His Ala Thr
            20                  25                  30

Ser Ser Thr His Asn Gly Ser His Thr Ser Arg Thr Thr Ser Ala Gln
        35                  40                  45

Thr Arg Ser Val Tyr Ser Gln His Val Thr Ser Ser Glu Ala Val Ser
    50                  55                  60

His Arg Ala Asn Glu Thr Ile Tyr Asn Thr Thr Leu Lys Tyr Gly Asp
65                  70                  75                  80

Val Val Gly Val Asn Thr Thr Lys Tyr Pro Tyr Arg Val Cys Ser Met
                85                  90                  95
```

```
Ala Gln Gly Thr Asp Leu Ile Arg Phe Glu Arg Asn Ile Ile Cys Thr
                100                 105                 110

Ser Met Lys Pro Ile Asn Glu Asp Leu Asp Glu Gly Ile Met Val Val
            115                 120                 125

Tyr Lys Arg Asn Ile Val Ala His Thr Phe Lys Val Arg Val Tyr Gln
        130                 135                 140

Lys Val Leu Thr Phe Arg Arg Ser Tyr Ala Tyr His Arg Thr Thr Tyr
145                 150                 155                 160

Leu Leu Gly Ser Asn Thr Glu Tyr Val Ala Pro Pro Met Trp Glu Ile
                165                 170                 175

His His Ile Asn Lys Phe Ala Gln Cys Tyr Ser Ser Tyr Ser Arg Val
            180                 185                 190

Ile Gly Gly Thr Val Phe Val Ala Tyr His Arg Asp Ser Tyr Glu Asn
        195                 200                 205

Lys Thr Met Gln Leu Ile Pro Asp Asp Tyr Ser Asn Thr His Ser Thr
210                 215                 220

Arg Tyr Val Thr Val Lys Asp Gln Trp His Ser Arg Gly Ser Glu Ala
225                 230                 235                 240

Leu Tyr Arg Glu Thr Cys Asn Leu Asn Cys Met Leu Thr Ile Thr Thr
                245                 250                 255

Ala Arg Ser Lys Tyr Pro Tyr His Phe Phe Ala Thr Ser Thr Gly Asp
            260                 265                 270

Val Val Tyr Ile Ser Pro Phe Tyr Asn Gly Thr Asn Arg Asn Ala Ser
        275                 280                 285

Tyr Phe Gly Glu Asn Ala Asp Lys Phe Phe Ile Phe Pro Asn Tyr Thr
        290                 295                 300

Ile Val Ser Asp Phe Gly Arg Pro Asn Ala Ala Pro Glu Thr His Arg
305                 310                 315                 320

Leu Val Ala Phe Leu Glu Arg Ala Asp Ser Val Ile Ser Trp Asp Ile
                325                 330                 335

Gln Asp Glu Lys Asn Val Thr Cys Gln Leu Thr Phe Trp Glu Ala Ser
            340                 345                 350

Glu Arg Thr Ile Arg Ser Glu Ala Glu Asp Ser Tyr His Phe Ser Ser
        355                 360                 365

Ala Lys Met Thr Ala Thr Phe Leu Ser Lys Lys Gln Glu Val Asn Met
        370                 375                 380

Ser Asp Ser Ala Leu Asp Cys Val Arg Asp Glu Ala Ile Asn Lys Leu
385                 390                 395                 400

Gln Gln Ile Phe Asn Thr Ser Tyr Asn Gln Thr Tyr Glu Lys Tyr Gly
                405                 410                 415

Asn Val Ser Val Phe Glu Thr Ser Gly Gly Leu Val Val Phe Trp Gln
            420                 425                 430

Gly Ile Lys Gln Lys Ser Leu Val Glu Leu Glu Arg Leu Ala Asn Arg
        435                 440                 445

Ser Ser Leu Asn Ile Thr His Thr Thr Gln Arg Ser Thr Ser Asp Asn
450                 455                 460

Asn Thr Thr His Leu Ser Ser Met Glu Ser Val His Asn Leu Val Tyr
465                 470                 475                 480

Ala Gln Leu Gln Phe Thr Tyr Asp Thr Leu Arg Gly Tyr Ile Asn Arg
                485                 490                 495

Ala Leu Ala Gln Ile Ala Glu Ala Trp Cys Val Asp Gln Arg Arg Thr
            500                 505                 510

Leu Glu Val Phe Lys Glu Leu Ser Lys Ile Asn Pro Ser Ala Ile Leu
```

```
            515                 520                 525
Ser Ala Ile Tyr Asn Lys Pro Ile Ala Ala Arg Phe Met Gly Asp Val
530                 535                 540

Leu Gly Leu Ala Ser Cys Val Thr Ile Asn Gln Thr Ser Val Lys Val
545                 550                 555                 560

Leu Arg Asp Met Asn Val Lys Glu Ser Pro Gly Arg Cys Tyr Ser Arg
                565                 570                 575

Pro Val Val Ile Phe Asn Phe Ala Asn Ser Ser Tyr Val Gln Tyr Gly
                580                 585                 590

Gln Leu Gly Glu Asp Asn Glu Ile Leu Leu Gly Asn His Arg Thr Glu
                595                 600                 605

Glu Cys Gln Leu Pro Ser Leu Lys Ile Phe Ile Ala Gly Asn Ser Ala
610                 615                 620

Tyr Glu Tyr Val Asp Tyr Leu Phe Lys Arg Met Ile Asp Leu Ser Ser
625                 630                 635                 640

Ile Ser Thr Val Asp Ser Met Ile Ala Leu Asp Ile Asp Pro Leu Glu
                645                 650                 655

Asn Thr Asp Phe Arg Val Leu Glu Leu Tyr Ser Gln Lys Glu Leu Arg
                660                 665                 670

Ser Ser Asn Val Phe Asp Leu Glu Glu Ile Met Arg Glu Phe Asn Ser
                675                 680                 685

Tyr Lys Gln Arg Val Lys Tyr Val Glu Asp Lys Val Val Asp Pro Leu
                690                 695                 700

Pro Pro
705

<210> SEQ ID NO 2
<211> LENGTH: 715
<212> TYPE: PRT
<213> ORGANISM: Human cytomegalovirus
<220> FEATURE:
<223> OTHER INFORMATION: gH ectodomain

<400> SEQUENCE: 2

Met Arg Pro Gly Leu Pro Ser Tyr Leu Ile Ile Leu Ala Val Cys Leu
1               5                   10                  15

Phe Ser His Leu Leu Ser Ser Arg Tyr Gly Ala Glu Ala Val Ser Glu
                20                  25                  30

Pro Leu Asp Lys Ala Phe His Leu Leu Leu Asn Thr Tyr Gly Arg Pro
                35                  40                  45

Ile Arg Phe Leu Arg Glu Asn Thr Thr Gln Cys Thr Tyr Asn Ser Ser
            50                  55                  60

Leu Arg Asn Ser Thr Val Val Arg Glu Asn Ala Ile Ser Phe Asn Phe
65              70                  75                  80

Phe Gln Ser Tyr Asn Gln Tyr Tyr Val Phe His Met Pro Arg Cys Leu
                85                  90                  95

Phe Ala Gly Pro Leu Ala Glu Gln Phe Leu Asn Gln Val Asp Leu Thr
                100                 105                 110

Glu Thr Leu Glu Arg Tyr Gln Gln Arg Leu Asn Thr Tyr Ala Leu Val
                115                 120                 125

Ser Lys Asp Leu Ala Ser Tyr Arg Ser Phe Ser Gln Gln Leu Lys Ala
                130                 135                 140

Gln Asp Ser Leu Gly Glu Gln Pro Thr Thr Val Pro Pro Pro Ile Asp
145                 150                 155                 160

Leu Ser Ile Pro His Val Trp Met Pro Pro Gln Thr Thr Pro His Gly
```

```
                    165                 170                 175
Trp Thr Glu Ser His Thr Thr Ser Gly Leu His Arg Pro His Phe Asn
                180                 185                 190
Gln Thr Cys Ile Leu Phe Asp Gly His Asp Leu Leu Phe Ser Thr Val
            195                 200                 205
Thr Pro Cys Leu His Gln Gly Phe Tyr Leu Ile Asp Glu Leu Arg Tyr
        210                 215                 220
Val Lys Ile Thr Leu Thr Glu Asp Phe Phe Val Val Thr Val Ser Ile
225                 230                 235                 240
Asp Asp Asp Thr Pro Met Leu Leu Ile Phe Gly His Leu Pro Arg Val
                245                 250                 255
Leu Phe Lys Ala Pro Tyr Gln Arg Asp Asn Phe Ile Leu Arg Gln Thr
            260                 265                 270
Glu Lys His Glu Leu Leu Val Leu Val Lys Lys Asp Gln Leu Asn Arg
        275                 280                 285
His Ser Tyr Leu Lys Asp Pro Asp Phe Leu Asp Ala Ala Leu Asp Phe
        290                 295                 300
Asn Tyr Leu Asp Leu Ser Ala Leu Leu Arg Asn Ser Phe His Arg Tyr
305                 310                 315                 320
Ala Val Asp Val Leu Lys Ser Gly Arg Cys Gln Met Leu Asp Arg Arg
                325                 330                 335
Thr Val Glu Met Ala Phe Ala Tyr Ala Leu Ala Leu Phe Ala Ala Ala
            340                 345                 350
Arg Gln Glu Glu Ala Gly Ala Gln Val Ser Val Pro Arg Ala Leu Asp
        355                 360                 365
Arg Gln Ala Ala Leu Leu Gln Ile Gln Glu Phe Met Ile Thr Cys Leu
        370                 375                 380
Ser Gln Thr Pro Pro Arg Thr Thr Leu Leu Leu Tyr Pro Thr Ala Val
385                 390                 395                 400
Asp Leu Ala Lys Arg Ala Leu Trp Thr Pro Asn Gln Ile Thr Asp Ile
                405                 410                 415
Thr Ser Leu Val Arg Leu Val Tyr Ile Leu Ser Lys Gln Asn Gln Gln
            420                 425                 430
His Leu Ile Pro Gln Trp Ala Leu Arg Gln Ile Ala Asp Phe Ala Leu
        435                 440                 445
Lys Leu His Lys Thr His Leu Ala Ser Phe Leu Ser Ala Phe Ala Arg
        450                 455                 460
Gln Glu Leu Tyr Leu Met Gly Ser Leu Val His Ser Met Leu Val His
465                 470                 475                 480
Thr Thr Glu Arg Arg Glu Ile Phe Ile Val Glu Thr Gly Leu Cys Ser
                485                 490                 495
Leu Ala Glu Leu Ser His Phe Thr Gln Leu Leu Ala His Pro His His
            500                 505                 510
Glu Tyr Leu Ser Asp Leu Tyr Thr Pro Cys Ser Ser Ser Gly Arg Arg
        515                 520                 525
Asp His Ser Leu Glu Arg Leu Thr Arg Leu Phe Pro Asp Ala Thr Val
        530                 535                 540
Pro Ala Thr Val Pro Ala Ala Leu Ser Ile Leu Ser Thr Met Gln Pro
545                 550                 555                 560
Ser Thr Leu Glu Thr Phe Pro Asp Leu Phe Cys Leu Pro Leu Gly Glu
                565                 570                 575
Ser Phe Ser Ala Leu Thr Val Ser Glu His Val Ser Tyr Ile Val Thr
            580                 585                 590
```

Asn Gln Tyr Leu Ile Lys Gly Ile Ser Tyr Pro Val Ser Thr Thr Val
            595                 600                 605

Val Gly Gln Ser Leu Ile Ile Thr Gln Thr Asp Ser Gln Thr Lys Cys
610                 615                 620

Glu Leu Thr Arg Asn Met His Thr Thr His Ser Ile Thr Val Ala Leu
625                 630                 635                 640

Asn Ile Ser Leu Glu Asn Cys Ala Phe Cys Gln Ser Ala Leu Leu Glu
            645                 650                 655

Tyr Asp Asp Thr Gln Gly Val Ile Asn Ile Met Tyr Met His Asp Ser
            660                 665                 670

Asp Asp Val Leu Phe Ala Leu Asp Pro Tyr Asn Glu Val Val Val Ser
            675                 680                 685

Ser Pro Arg Thr His Tyr Leu Met Leu Leu Lys Asn Gly Thr Val Leu
            690                 695                 700

Glu Val Thr Asp Val Val Val Asp Ala Thr Asp
705                 710                 715

<210> SEQ ID NO 3
<211> LENGTH: 278
<212> TYPE: PRT
<213> ORGANISM: Human cytomegalovirus
<220> FEATURE:
<223> OTHER INFORMATION: gL

<400> SEQUENCE: 3

Met Cys Arg Arg Pro Asp Cys Gly Phe Ser Phe Ser Pro Gly Pro Val
1               5                   10                  15

Ile Leu Leu Trp Cys Cys Leu Leu Leu Pro Ile Val Ser Ser Ala Ala
            20                  25                  30

Val Ser Val Ala Pro Thr Ala Ala Glu Lys Val Pro Ala Glu Cys Pro
        35                  40                  45

Glu Leu Thr Arg Arg Cys Leu Leu Gly Glu Val Phe Glu Gly Asp Lys
    50                  55                  60

Tyr Glu Ser Trp Leu Arg Pro Leu Val Asn Val Thr Gly Arg Asp Gly
65                  70                  75                  80

Pro Leu Ser Gln Leu Ile Arg Tyr Arg Pro Val Thr Pro Glu Ala Ala
                85                  90                  95

Asn Ser Val Leu Leu Asp Glu Ala Phe Leu Asp Thr Leu Ala Leu Leu
            100                 105                 110

Tyr Asn Asn Pro Asp Gln Leu Arg Ala Leu Leu Thr Leu Leu Ser Ser
        115                 120                 125

Asp Thr Ala Pro Arg Trp Met Thr Val Met Arg Gly Tyr Ser Glu Cys
    130                 135                 140

Gly Asp Gly Ser Pro Ala Val Tyr Thr Cys Val Asp Asp Leu Cys Arg
145                 150                 155                 160

Gly Tyr Asp Leu Thr Arg Leu Ser Tyr Gly Arg Ser Ile Phe Thr Glu
                165                 170                 175

His Val Leu Gly Phe Glu Leu Val Pro Pro Ser Leu Phe Asn Val Val
            180                 185                 190

Val Ala Ile Arg Asn Glu Ala Thr Arg Thr Asn Arg Ala Val Arg Leu
        195                 200                 205

Pro Val Ser Thr Ala Ala Ala Pro Glu Gly Ile Thr Leu Phe Tyr Gly
    210                 215                 220

Leu Tyr Asn Ala Val Lys Glu Phe Cys Leu Arg His Gln Leu Asp Pro
225                 230                 235                 240

```
Pro Leu Leu Arg His Leu Asp Lys Tyr Tyr Ala Gly Leu Pro Pro Glu
            245                 250                 255

Leu Lys Gln Thr Arg Val Asn Leu Pro Ala His Ser Arg Tyr Gly Pro
            260                 265                 270

Gln Ala Val Asp Ala Arg
        275

<210> SEQ ID NO 4
<211> LENGTH: 171
<212> TYPE: PRT
<213> ORGANISM: Human cytomegalovirus
<220> FEATURE:
<223> OTHER INFORMATION: UL128

<400> SEQUENCE: 4

Met Ser Pro Lys Asp Leu Thr Pro Phe Leu Thr Ala Leu Trp Leu Leu
1               5                   10                  15

Leu Gly His Ser Arg Val Pro Arg Val Arg Ala Glu Glu Cys Cys Glu
            20                  25                  30

Phe Ile Asn Val Asn His Pro Pro Glu Arg Cys Tyr Asp Phe Lys Met
        35                  40                  45

Cys Asn Arg Phe Thr Val Ala Leu Arg Cys Pro Asp Gly Glu Val Cys
    50                  55                  60

Tyr Ser Pro Glu Lys Thr Ala Glu Ile Arg Gly Ile Val Thr Thr Met
65                  70                  75                  80

Thr His Ser Leu Thr Arg Gln Val Val His Asn Lys Leu Thr Ser Cys
                85                  90                  95

Asn Tyr Asn Pro Leu Tyr Leu Glu Ala Asp Gly Arg Ile Arg Cys Gly
            100                 105                 110

Lys Val Asn Asp Lys Ala Gln Tyr Leu Leu Gly Ala Ala Gly Ser Val
        115                 120                 125

Pro Tyr Arg Trp Ile Asn Leu Glu Tyr Asp Lys Ile Thr Arg Ile Val
    130                 135                 140

Gly Leu Asp Gln Tyr Leu Glu Ser Val Lys Lys His Lys Arg Leu Asp
145                 150                 155                 160

Val Cys Arg Ala Lys Met Gly Tyr Met Leu Gln
                165                 170

<210> SEQ ID NO 5
<211> LENGTH: 214
<212> TYPE: PRT
<213> ORGANISM: Human cytomegalovirus
<220> FEATURE:
<223> OTHER INFORMATION: UL130

<400> SEQUENCE: 5

Met Leu Arg Leu Leu Arg His His Phe His Cys Leu Leu Leu Cys
1               5                   10                  15

Ala Val Trp Ala Thr Pro Cys Leu Ala Ser Pro Trp Ser Thr Leu Thr
            20                  25                  30

Ala Asn Gln Asn Pro Ser Pro Pro Trp Ser Lys Leu Thr Tyr Ser Lys
        35                  40                  45

Pro His Asp Ala Ala Thr Phe Tyr Cys Pro Phe Leu Tyr Pro Ser Pro
    50                  55                  60

Pro Arg Ser Pro Leu Gln Phe Ser Gly Phe Gln Arg Val Ser Thr Gly
65                  70                  75                  80

Pro Glu Cys Arg Asn Glu Thr Leu Tyr Leu Leu Tyr Asn Arg Glu Gly
```

```
                85                  90                  95
Gln Thr Leu Val Glu Arg Ser Ser Thr Trp Val Lys Val Ile Trp
            100                 105                 110
Tyr Leu Ser Gly Arg Asn Gln Thr Ile Leu Gln Arg Met Pro Arg Thr
            115                 120                 125
Ala Ser Lys Pro Ser Asp Gly Asn Val Gln Ile Ser Val Glu Asp Ala
            130                 135                 140
Lys Ile Phe Gly Ala His Met Val Pro Lys Gln Thr Lys Leu Leu Arg
145                 150                 155                 160
Phe Val Val Asn Asp Gly Thr Arg Tyr Gln Met Cys Val Met Lys Leu
                165                 170                 175
Glu Ser Trp Ala His Val Phe Arg Asp Tyr Ser Val Ser Phe Gln Val
            180                 185                 190
Arg Leu Thr Phe Thr Glu Ala Asn Asn Gln Thr Tyr Thr Phe Cys Thr
            195                 200                 205
His Pro Asn Leu Ile Val
        210

<210> SEQ ID NO 6
<211> LENGTH: 129
<212> TYPE: PRT
<213> ORGANISM: Human cytomegalovirus
<220> FEATURE:
<223> OTHER INFORMATION: UL131

<400> SEQUENCE: 6

Met Arg Leu Cys Arg Val Trp Leu Ser Val Cys Leu Cys Ala Val Val
1               5                   10                  15
Leu Gly Gln Cys Gln Arg Glu Thr Ala Glu Lys Asn Asp Tyr Tyr Arg
            20                  25                  30
Val Pro His Tyr Trp Asp Ala Cys Ser Arg Ala Leu Pro Asp Gln Thr
        35                  40                  45
Arg Tyr Lys Tyr Val Glu Gln Leu Val Asp Leu Thr Leu Asn Tyr His
    50                  55                  60
Tyr Asp Ala Ser His Gly Leu Asp Asn Phe Asp Val Leu Lys Arg Ile
65                  70                  75                  80
Asn Val Thr Glu Val Ser Leu Leu Ile Ser Asp Phe Arg Arg Gln Asn
                85                  90                  95
Arg Arg Gly Gly Thr Asn Lys Arg Thr Thr Phe Asn Ala Ala Gly Ser
            100                 105                 110
Leu Ala Pro His Ala Arg Ser Leu Glu Phe Ser Val Arg Leu Phe Ala
            115                 120                 125
Asn

<210> SEQ ID NO 7
<211> LENGTH: 906
<212> TYPE: PRT
<213> ORGANISM: Human cytomegalovirus
<220> FEATURE:
<223> OTHER INFORMATION: HCMV AD169 gB

<400> SEQUENCE: 7

Met Glu Ser Arg Ile Trp Cys Leu Val Val Cys Val Asn Leu Cys Ile
1               5                   10                  15
Val Cys Leu Gly Ala Ala Val Ser Ser Ser Ser Thr His Ala Thr
            20                  25                  30
Ser Ser Thr His Asn Gly Ser His Thr Ser Arg Thr Thr Ser Ala Gln
```

-continued

```
                35                  40                  45
Thr Arg Ser Val Tyr Ser Gln His Val Thr Ser Ser Glu Ala Val Ser
 50                  55                  60
His Arg Ala Asn Glu Thr Ile Tyr Asn Thr Thr Leu Lys Tyr Gly Asp
 65                  70                  75                  80
Val Val Gly Val Asn Thr Thr Lys Tyr Pro Tyr Arg Val Cys Ser Met
                 85                  90                  95
Ala Gln Gly Thr Asp Leu Ile Arg Phe Glu Arg Asn Ile Ile Cys Thr
                100                 105                 110
Ser Met Lys Pro Ile Asn Glu Asp Leu Asp Glu Gly Ile Met Val Val
            115                 120                 125
Tyr Lys Arg Asn Ile Val Ala His Thr Phe Lys Val Arg Val Tyr Gln
130                 135                 140
Lys Val Leu Thr Phe Arg Arg Ser Tyr Ala Tyr Ile Tyr Thr Thr Tyr
145                 150                 155                 160
Leu Leu Gly Ser Asn Thr Glu Tyr Val Ala Pro Pro Met Trp Glu Ile
                165                 170                 175
His His Ile Asn Lys Phe Ala Gln Cys Tyr Ser Ser Tyr Ser Arg Val
            180                 185                 190
Ile Gly Gly Thr Val Phe Val Ala Tyr His Arg Asp Ser Tyr Glu Asn
            195                 200                 205
Lys Thr Met Gln Leu Ile Pro Asp Asp Tyr Ser Asn Thr His Ser Thr
210                 215                 220
Arg Tyr Val Thr Val Lys Asp Gln Trp His Ser Arg Gly Ser Thr Trp
225                 230                 235                 240
Leu Tyr Arg Glu Thr Cys Asn Leu Asn Cys Met Leu Thr Ile Thr Thr
                245                 250                 255
Ala Arg Ser Lys Tyr Pro Tyr His Phe Ala Thr Ser Thr Gly Asp
            260                 265                 270
Val Val Tyr Ile Ser Pro Phe Tyr Asn Gly Thr Asn Arg Asn Ala Ser
            275                 280                 285
Tyr Phe Gly Glu Asn Ala Asp Lys Phe Phe Ile Phe Pro Asn Tyr Thr
290                 295                 300
Ile Val Ser Asp Phe Gly Arg Pro Asn Ala Ala Pro Glu Thr His Arg
305                 310                 315                 320
Leu Val Ala Phe Leu Glu Arg Ala Asp Ser Val Ile Ser Trp Asp Ile
                325                 330                 335
Gln Asp Glu Lys Asn Val Thr Cys Gln Leu Thr Phe Trp Glu Ala Ser
            340                 345                 350
Glu Arg Thr Ile Arg Ser Glu Ala Glu Asp Ser Tyr His Phe Ser Ser
            355                 360                 365
Ala Lys Met Thr Ala Thr Phe Leu Ser Lys Lys Gln Glu Val Asn Met
370                 375                 380
Ser Asp Ser Ala Leu Asp Cys Val Arg Asp Glu Ala Ile Asn Lys Leu
385                 390                 395                 400
Gln Gln Ile Phe Asn Thr Ser Tyr Asn Gln Thr Tyr Glu Lys Tyr Gly
                405                 410                 415
Asn Val Ser Val Phe Glu Thr Ser Gly Gly Leu Val Val Phe Trp Gln
            420                 425                 430
Gly Ile Lys Gln Lys Ser Leu Val Glu Leu Glu Arg Leu Ala Asn Arg
            435                 440                 445
Ser Ser Leu Asn Ile Thr His Arg Thr Arg Arg Ser Thr Ser Asp Asn
450                 455                 460
```

```
Asn Thr Thr His Leu Ser Ser Met Glu Ser Val His Asn Leu Val Tyr
465                 470                 475                 480

Ala Gln Leu Gln Phe Thr Tyr Asp Thr Leu Arg Gly Tyr Ile Asn Arg
            485                 490                 495

Ala Leu Ala Gln Ile Ala Glu Ala Trp Cys Val Asp Gln Arg Arg Thr
        500                 505                 510

Leu Glu Val Phe Lys Glu Leu Ser Lys Ile Asn Pro Ser Ala Ile Leu
    515                 520                 525

Ser Ala Ile Tyr Asn Lys Pro Ile Ala Arg Phe Met Gly Asp Val
530                 535                 540

Leu Gly Leu Ala Ser Cys Val Thr Ile Asn Gln Thr Ser Val Lys Val
545                 550                 555                 560

Leu Arg Asp Met Asn Val Lys Glu Ser Pro Gly Arg Cys Tyr Ser Arg
                565                 570                 575

Pro Val Val Ile Phe Asn Phe Ala Asn Ser Ser Tyr Val Gln Tyr Gly
            580                 585                 590

Gln Leu Gly Glu Asp Asn Glu Ile Leu Leu Gly Asn His Arg Thr Glu
        595                 600                 605

Glu Cys Gln Leu Pro Ser Leu Lys Ile Phe Ile Ala Gly Asn Ser Ala
    610                 615                 620

Tyr Glu Tyr Val Asp Tyr Leu Phe Lys Arg Met Ile Asp Leu Ser Ser
625                 630                 635                 640

Ile Ser Thr Val Asp Ser Met Ile Ala Leu Asp Ile Asp Pro Leu Glu
                645                 650                 655

Asn Thr Asp Phe Arg Val Leu Glu Leu Tyr Ser Gln Lys Glu Leu Arg
            660                 665                 670

Ser Ser Asn Val Phe Asp Leu Glu Glu Ile Met Arg Glu Phe Asn Ser
        675                 680                 685

Tyr Lys Gln Arg Val Lys Tyr Val Glu Asp Lys Val Val Asp Pro Leu
690                 695                 700

Pro Pro Tyr Leu Lys Gly Leu Asp Asp Leu Met Ser Gly Leu Gly Ala
705                 710                 715                 720

Ala Gly Lys Ala Val Gly Val Ala Ile Gly Ala Val Gly Gly Ala Val
                725                 730                 735

Ala Ser Val Val Glu Gly Val Ala Thr Phe Leu Lys Asn Pro Phe Gly
            740                 745                 750

Ala Phe Thr Ile Ile Leu Val Ala Ile Ala Val Val Ile Ile Thr Tyr
        755                 760                 765

Leu Ile Tyr Thr Arg Gln Arg Arg Leu Cys Thr Gln Pro Leu Gln Asn
770                 775                 780

Leu Phe Pro Tyr Leu Val Ser Ala Asp Gly Thr Thr Val Thr Ser Gly
785                 790                 795                 800

Ser Thr Lys Asp Thr Ser Leu Gln Ala Pro Pro Ser Tyr Glu Glu Ser
                805                 810                 815

Val Tyr Asn Ser Gly Arg Lys Gly Pro Gly Pro Pro Ser Ser Asp Ala
            820                 825                 830

Ser Thr Ala Ala Pro Pro Tyr Thr Asn Glu Gln Ala Tyr Gln Met Leu
        835                 840                 845

Leu Ala Leu Ala Arg Leu Asp Ala Glu Gln Arg Ala Gln Gln Asn Gly
    850                 855                 860

Thr Asp Ser Leu Asp Gly Gln Thr Gly Thr Gln Asp Lys Gly Gln Lys
865                 870                 875                 880
```

Pro Asn Leu Leu Asp Arg Leu Arg His Arg Lys Asn Gly Tyr Arg His
            885                 890                 895

Leu Lys Asp Ser Asp Glu Glu Glu Asn Val
            900                 905

<210> SEQ ID NO 8
<211> LENGTH: 900
<212> TYPE: PRT
<213> ORGANISM: Guinea pig cytomegalovirus
<220> FEATURE:
<223> OTHER INFORMATION: GPCMV 22122 gB

<400> SEQUENCE: 8

Met Arg Pro Val Arg Gly Ile Ala Arg Ser Arg Ile Leu Ser Cys Ser
1               5                   10                  15

Trp Arg Gly Thr Trp Thr Ser Ala Leu Thr Ile Leu Tyr Leu Gly Val
            20                  25                  30

Tyr Cys Glu Ser Thr Thr Val Thr Pro Thr Val Glu Asp Thr Thr
            35                  40                  45

Val Ser Asn Gly Asn His Ser Asp Ala Ser Arg Asn Asn Thr Val Ile
    50                  55                  60

Arg Asn Leu Thr Ala Ser Val Asp Phe Ser Gln Arg Lys Leu Tyr Pro
65                  70                  75                  80

Tyr Arg Ile Cys Ser Met Ser Met Gly Thr Asp Leu Val Arg Phe Ala
                85                  90                  95

Arg Thr Ile Gln Cys Val Pro Phe Asn Pro Arg Val Asn Ser Glu Glu
            100                 105                 110

Gly Ile Met Leu Ile Tyr Lys Arg Asn Ile Leu Pro Tyr Val Phe Thr
            115                 120                 125

Ala Tyr Thr Tyr Gln Lys Glu Leu Leu Phe Gln Arg Ser Tyr Lys Tyr
    130                 135                 140

Val Thr Tyr Asp Tyr Leu Leu Gly Tyr Ser Arg Glu Phe Val Ala Leu
145                 150                 155                 160

Pro Met Trp Glu Ile Phe Leu Val Asn Ser Arg Gly Gln Cys Tyr Thr
                165                 170                 175

Ser His Gln Arg Val Ile Gly Ala Asp Arg Tyr Ile Ala Tyr His Asn
            180                 185                 190

Asp Asn Glu Val Asn Glu Thr Met Trp Leu Met Arg Asp Asp Met Gly
            195                 200                 205

Asn Asp Asp Thr Tyr Arg Tyr Ile Thr Val Lys Glu His Ala Arg Thr
    210                 215                 220

Pro Gly Ser Val Trp Leu Tyr Lys Glu Thr Cys Ser Met Asn Cys Ile
225                 230                 235                 240

Val Thr Lys Thr Lys Gly Lys Ser Lys Phe Pro Tyr Asp Met Phe Val
                245                 250                 255

Leu Pro Ser Gly Val Ile Val Asn Ile Ser Pro Phe Tyr Asn Gly Ser
            260                 265                 270

Asn Gly Lys Thr Phe Arg Glu Gln Arg Glu Lys Phe His Ile Trp Ser
            275                 280                 285

Asn Tyr Ser Ile Leu Lys Asp Phe Gly Ser Arg Ala Leu Glu Ala Arg
    290                 295                 300

Ile Val Pro Lys Met Ala Phe Tyr Glu Arg Glu Asp Val Val Ile Gly
305                 310                 315                 320

Trp Glu Val Asn Asp Gln Ser Asn Val Thr Cys Glu Met Ile Leu Trp
                325                 330                 335

Glu Thr Val Asp Arg Ala Ile Arg Thr Glu Tyr Glu Asn Ala Phe His
            340                 345                 350

Tyr Val Ala Arg Thr Leu Thr Ser Thr Phe Val Glu Asn Lys Tyr Ser
            355                 360                 365

Pro Asp Asn Asn Leu Thr Glu Asp Asp Ile Lys Cys Phe Lys Asn Asp
            370                 375                 380

Ala Gln Lys Lys Ile Glu Glu Val Phe Leu Arg Asp Tyr Asn Glu Thr
385                 390                 395                 400

Tyr Asp Met Asp Gly Asn Ala Thr Tyr His Val Thr Thr Gly Gly Leu
                405                 410                 415

Val Ile Val Trp Gln Gly Leu Lys Gln Lys Ser Leu Lys Ala Leu Glu
            420                 425                 430

Ile Ala Ala Asn Glu Ser Ala Val Ser Ala Thr Gly Ser Asn Ser Arg
            435                 440                 445

Arg Lys Arg Ser Leu Pro Asp Glu Ser Thr Gly Asp Ile Ser Tyr Ala
            450                 455                 460

Gln Leu Gln Phe Ala Tyr Asp Thr Leu Arg Thr Tyr Ile Asn Gln Ala
465                 470                 475                 480

Leu Gly His Ile Ala Glu Ala Trp Cys Leu Asp Gln Lys Arg Thr Ala
                485                 490                 495

Glu Val Leu His Glu Leu Ser Lys Ile Asn Pro Ser Asn Ile Leu Ser
            500                 505                 510

Ala Ile Phe Gly Val Pro Val Ala Arg Val Val Gly Asp Val Ile
            515                 520                 525

Ser Leu Ala Lys Cys Ile Glu Val Asn Gln Ser Thr Val Leu Ile Lys
530                 535                 540

Gly Asp Met Arg Lys Phe Ser Asp Asp Gly Lys Leu Glu Gly Cys Tyr
545                 550                 555                 560

Ser Arg Pro Val Val Trp Phe Ser Met Lys Asn Ser Thr Glu Val Arg
                565                 570                 575

Leu Gly Gln Leu Gly Glu Asp Asn Glu Ile Leu Leu Gly Thr His Arg
            580                 585                 590

Met Glu Thr Cys Gln Thr Gln Asp Tyr Arg Ile Phe Val Ala Gly Asp
            595                 600                 605

Ile Gly Tyr Glu Phe Gln Gln Tyr Val Phe Thr Lys Lys Ile Asn Leu
            610                 615                 620

Ser Glu Ile Asp Ile Ile Asp Thr Met Ile Ala Leu Lys Thr Glu Pro
625                 630                 635                 640

Leu Glu Asn Ile Asp Phe Lys Val Leu Glu Leu Tyr Ser Arg Asp Glu
                645                 650                 655

Leu Ala Gln Ala Asn Val Phe Asp Leu Glu Ser Ile Met Arg Glu Tyr
            660                 665                 670

Asn Tyr Gln Lys Lys Arg Leu Asp Phe Val Val Glu Arg Val Ile Asn
            675                 680                 685

Pro Ile Pro Pro Ala Leu Lys Gly Leu Asp Glu Met Met Asn Gly Met
            690                 695                 700

Gly Ala Ile Gly Lys Gly Ile Gly Glu Ala Val Gly Ala Val Gly Gly
705                 710                 715                 720

Ala Ile Gly Ser Phe Ile Gly Ala Leu Val Thr Phe Val Thr Asn Pro
                725                 730                 735

Phe Gly Ala Phe Val Val Phe Leu Phe Cys Val Gly Cys Ile Thr Leu
            740                 745                 750

Val Ile Thr Val Tyr Arg Arg Gln Arg Arg Ala Met Gln Arg Pro Phe

```
                755                 760                 765
Asp Tyr Phe Pro Tyr Ala Ser Gln Thr Ile Thr Ser Ser Val Ala
    770                 775                 780

Asp Ser Ser Ile Ala Val Ala Tyr Pro Gly Pro Glu Gly Thr Ser Gly
785                 790                 795                 800

Asp Ala Pro Pro Tyr Pro Gly Glu Ala Pro Tyr Gly Tyr Lys Asp
                805                 810                 815

Leu Ser Val Asp Ala Asp Thr Arg Val Ser Ser Ser Ala Gly Ala
            820                 825                 830

Gly Ala Asp Phe Asn Glu Glu Asp Ala Val Arg Met Leu Arg Ala Ile
                835                 840                 845

Lys Arg Leu Asp Asp Lys Lys Arg Gln Glu Ile Glu Lys Ser Ser Lys
            850                 855                 860

Asp Ser Ala Ser Asn Lys Asn Ser Glu Thr Arg Arg Pro Gly Ile
865                 870                 875                 880

Met Asp Arg Leu Arg Arg Gly Gly Tyr Gln Lys Leu Asn Thr Glu
                885                 890                 895

Asp Asp Val His
            900

<210> SEQ ID NO 9
<211> LENGTH: 742
<212> TYPE: PRT
<213> ORGANISM: Human cytomegalovirus
<220> FEATURE:
<223> OTHER INFORMATION: gH

<400> SEQUENCE: 9

Met Arg Pro Gly Leu Pro Ser Tyr Leu Ile Ile Leu Ala Val Cys Leu
1               5                   10                  15

Phe Ser His Leu Leu Ser Ser Arg Tyr Gly Ala Glu Ala Val Ser Glu
                20                  25                  30

Pro Leu Asp Lys Ala Phe His Leu Leu Leu Asn Thr Tyr Gly Arg Pro
            35                  40                  45

Ile Arg Phe Leu Arg Glu Asn Thr Thr Gln Cys Thr Tyr Asn Ser Ser
        50                  55                  60

Leu Arg Asn Ser Thr Val Val Arg Glu Asn Ala Ile Ser Phe Asn Phe
65                  70                  75                  80

Phe Gln Ser Tyr Asn Gln Tyr Tyr Val Phe His Met Pro Arg Cys Leu
                    85                  90                  95

Phe Ala Gly Pro Leu Ala Glu Gln Phe Leu Asn Gln Val Asp Leu Thr
                100                 105                 110

Glu Thr Leu Glu Arg Tyr Gln Gln Arg Leu Asn Thr Tyr Ala Leu Val
            115                 120                 125

Ser Lys Asp Leu Ala Ser Tyr Arg Ser Phe Ser Gln Gln Leu Lys Ala
130                 135                 140

Gln Asp Ser Leu Gly Glu Gln Pro Thr Thr Val Pro Pro Pro Ile Asp
145                 150                 155                 160

Leu Ser Ile Pro His Val Trp Met Pro Pro Gln Thr Thr Pro His Gly
                165                 170                 175

Trp Thr Glu Ser His Thr Thr Ser Gly Leu His Arg Pro His Phe Asn
                180                 185                 190

Gln Thr Cys Ile Leu Phe Asp Gly His Asp Leu Leu Phe Ser Thr Val
            195                 200                 205

Thr Pro Cys Leu His Gln Gly Phe Tyr Leu Ile Asp Glu Leu Arg Tyr
```

```
                210                 215                 220
Val Lys Ile Thr Leu Thr Glu Asp Phe Phe Val Thr Val Ser Ile
225                 230                 235                 240

Asp Asp Asp Thr Pro Met Leu Leu Ile Phe Gly His Leu Pro Arg Val
                    245                 250                 255

Leu Phe Lys Ala Pro Tyr Gln Arg Asp Asn Phe Ile Leu Arg Gln Thr
                260                 265                 270

Glu Lys His Glu Leu Leu Val Leu Val Lys Lys Asp Gln Leu Asn Arg
                275                 280                 285

His Ser Tyr Leu Lys Asp Pro Asp Phe Leu Asp Ala Ala Leu Asp Phe
                290                 295                 300

Asn Tyr Leu Asp Leu Ser Ala Leu Leu Arg Asn Ser Phe His Arg Tyr
305                 310                 315                 320

Ala Val Asp Val Leu Lys Ser Gly Arg Cys Gln Met Leu Asp Arg Arg
                    325                 330                 335

Thr Val Glu Met Ala Phe Ala Tyr Ala Leu Ala Leu Phe Ala Ala Ala
                340                 345                 350

Arg Gln Glu Glu Ala Gly Ala Gln Val Ser Val Pro Arg Ala Leu Asp
                355                 360                 365

Arg Gln Ala Ala Leu Leu Gln Ile Gln Glu Phe Met Ile Thr Cys Leu
                370                 375                 380

Ser Gln Thr Pro Pro Arg Thr Thr Leu Leu Tyr Pro Thr Ala Val
385                 390                 395                 400

Asp Leu Ala Lys Arg Ala Leu Trp Thr Pro Asn Gln Ile Thr Asp Ile
                    405                 410                 415

Thr Ser Leu Val Arg Leu Val Tyr Ile Leu Ser Lys Gln Asn Gln Gln
                    420                 425                 430

His Leu Ile Pro Gln Trp Ala Leu Arg Gln Ile Ala Asp Phe Ala Leu
                435                 440                 445

Lys Leu His Lys Thr His Leu Ala Ser Phe Leu Ser Ala Phe Ala Arg
450                 455                 460

Gln Glu Leu Tyr Leu Met Gly Ser Leu Val His Ser Met Leu Val His
465                 470                 475                 480

Thr Thr Glu Arg Arg Glu Ile Phe Ile Val Glu Thr Gly Leu Cys Ser
                    485                 490                 495

Leu Ala Glu Leu Ser His Phe Thr Gln Leu Leu Ala His Pro His His
                500                 505                 510

Glu Tyr Leu Ser Asp Leu Tyr Thr Pro Cys Ser Ser Gly Arg Arg
                515                 520                 525

Asp His Ser Leu Glu Arg Leu Thr Arg Leu Phe Pro Asp Ala Thr Val
                530                 535                 540

Pro Ala Thr Val Pro Ala Leu Ser Ile Leu Ser Thr Met Gln Pro
545                 550                 555                 560

Ser Thr Leu Glu Thr Phe Pro Asp Leu Phe Cys Leu Pro Leu Gly Glu
                    565                 570                 575

Ser Phe Ser Ala Leu Thr Val Ser Glu His Val Ser Tyr Ile Val Thr
                580                 585                 590

Asn Gln Tyr Leu Ile Lys Gly Ile Ser Tyr Pro Val Ser Thr Thr Val
                595                 600                 605

Val Gly Gln Ser Leu Ile Ile Thr Gln Thr Asp Ser Gln Thr Lys Cys
                610                 615                 620

Glu Leu Thr Arg Asn Met His Thr Thr His Ser Ile Thr Val Ala Leu
625                 630                 635                 640
```

-continued

```
Asn Ile Ser Leu Glu Asn Cys Ala Phe Cys Gln Ser Ala Leu Leu Glu
            645                 650                 655

Tyr Asp Asp Thr Gln Gly Val Ile Asn Ile Met Tyr Met His Asp Ser
        660                 665                 670

Asp Asp Val Leu Phe Ala Leu Asp Pro Tyr Asn Glu Val Val Val Ser
            675                 680                 685

Ser Pro Arg Thr His Tyr Leu Met Leu Lys Asn Gly Thr Val Leu
690                 695                 700

Glu Val Thr Asp Val Val Asp Ala Thr Asp Ser Arg Leu Leu Met
705                 710                 715                 720

Met Ser Val Tyr Ala Leu Ser Ala Ile Ile Gly Ile Tyr Leu Leu Tyr
            725                 730                 735

Arg Met Leu Lys Thr Cys
            740

<210> SEQ ID NO 10
<211> LENGTH: 723
<212> TYPE: PRT
<213> ORGANISM: Guinea pig cytomegalovirus
<220> FEATURE:
<223> OTHER INFORMATION: GP75

<400> SEQUENCE: 10

Met Ser Pro Ala Thr Arg Phe Thr Val Ile Ser Cys Leu Val Val Ser
1               5                   10                  15

Leu Ile Thr Pro Ser Glu Thr Ser Ser Trp Phe Asp Pro Phe Ile Glu
            20                  25                  30

Trp Ala Arg Ser Ser Pro Asn Met Thr Cys Val Asn Asn Arg Thr Gly
        35                  40                  45

Thr Arg Ser Leu Ala Thr Glu Gly Leu Ile Ser Phe Asn Phe Tyr Glu
    50                  55                  60

Ala Ser Arg Thr Val Arg Thr Tyr Gln Val Pro Lys Cys Ile Phe Met
65                  70                  75                  80

Ser Ser Val Ser Lys Thr Ile Met Gln Gly Val Asp Leu Phe Glu Ser
                85                  90                  95

Leu Glu Ser Tyr Arg Arg Tyr Tyr Ser Tyr Ile Ile Val Pro Val
            100                 105                 110

His Ala Ser Phe Gln Ile Phe Ile His Asp Leu Arg Thr Asp Leu Ser
        115                 120                 125

Ser Pro Thr Glu Glu Leu Thr Ser Pro Val Asp Lys Thr Leu Pro Asn
    130                 135                 140

Val Thr Ile Trp His Thr Pro Ser Gly Tyr Val Ile Arg Leu Leu Asp
145                 150                 155                 160

Val Val Thr Pro Arg Phe Glu Glu Cys Thr Leu Phe Pro Asn His Thr
                165                 170                 175

Val Ile Phe Asp Met Thr Val Pro Cys Ser Gln Glu Val Tyr Leu Arg
            180                 185                 190

Gln Thr Gly Lys His Gln Phe Ala Ile Val Leu Thr Phe Thr Pro Ser
        195                 200                 205

Phe Phe Val Leu Asn Ile Gln Thr Ala Gln His Gln His Val Thr Glu
    210                 215                 220

Asn Asp Glu Asp Val Ile Leu Ile Phe Gly Asp Val Arg Ser Ile Asp
225                 230                 235                 240

Val Lys Ala Pro Tyr Ser Lys Pro Val Leu Thr Leu Arg Gln Ser Tyr
                245                 250                 255
```

```
Arg Asp Asp Leu Leu Ile Val Ala Lys Thr Ser Ile Val Asn Ala Thr
            260                 265                 270

Tyr Pro Phe Ile Lys Thr Gln Asp Phe Leu Lys Gly Thr Leu Ser Gly
        275                 280                 285

Asn Tyr Leu Asp Phe Asn His Val Tyr Thr Glu Phe Asn Arg Leu Val
    290                 295                 300

Ile His Asn Leu Val Glu Gly Leu Cys Asp Ala Pro Pro Asp Asp Arg
305                 310                 315                 320

Thr Val Ser Met Val Phe Ser Tyr Ala Val Leu Ala Arg Thr Leu Tyr
                325                 330                 335

His Thr Ser Asn Val Thr Ala Arg Leu Glu Asp Val Ala Leu Arg Tyr
            340                 345                 350

Val Arg Leu Thr Leu Ala Arg Thr Phe Leu Gln Gln Cys Phe Asp Val
        355                 360                 365

Gly Pro Arg Tyr Met Arg Phe Pro Thr Ile Asp Gly Ala Leu Ser Val
    370                 375                 380

Leu Leu Lys Leu Ile Arg Asn Ser Arg Asp Val Asp Gly Gly Leu Lys
385                 390                 395                 400

Leu Ser Leu Thr Phe Ala Leu Ile Phe Gly Asn Asn Thr Asp Met Thr
                405                 410                 415

Lys Glu Arg Asp Leu Glu Asn Ala Leu Tyr Glu Met Lys Ser Ile His
            420                 425                 430

Arg Ala Gly Leu Val Ser Pro Leu Ser Pro Arg Gln Arg Ser Leu Leu
        435                 440                 445

Tyr Met Met Ala Tyr Val Thr His His Thr Thr Ala Phe Pro Asp Ile
    450                 455                 460

Arg Arg Glu Met Leu Ala Met Gln Thr Ser Leu Cys Ser Pro Gln Glu
465                 470                 475                 480

Leu Tyr Asn Trp Ala Pro His Val Ser Ser Ala Gly Leu Thr Met Gln
                485                 490                 495

Glu Met Phe Thr Pro Cys Ser Gly Ser Gly Arg Arg Asp Tyr Ser Glu
            500                 505                 510

Ala Arg Ile Ala Glu Ile Val Gln Leu Asn Pro Leu Thr Thr Lys Thr
        515                 520                 525

Pro Ala Asp Leu Tyr Arg Ile Leu Ala His Phe Asp Arg Ser Asn Leu
    530                 535                 540

Thr Asn Phe Pro Ala Leu Ser Cys Ile Ser His Leu Ser Gly Tyr Val
545                 550                 555                 560

Ala Val Thr Leu Arg Asp Val Thr Tyr Val Val Ser Asn Val Met
                565                 570                 575

Leu Lys Gly Thr Ser Tyr Pro Val Thr Asn Leu Ala Val Asp Lys Thr
            580                 585                 590

Met Ile Val Thr Val Ser Pro Ala Gln His Pro Cys Glu Lys Thr Glu
        595                 600                 605

Val Ala His Ala Thr Arg Ser Ile Pro Ile Val Lys Asn Ile Thr Ile
    610                 615                 620

Gly Asn Asp Cys Glu Tyr Cys Lys Ser Ala Ile Met Glu Tyr Asp Glu
625                 630                 635                 640

Val Asn Gly Leu Ser Asn Ile Val Tyr Leu Ala Asp Thr Ala Asp Leu
                645                 650                 655

Val Leu Val Thr Asn Leu Asp Asn Arg Ile Leu Ala Ser Ser Pro Arg
            660                 665                 670
```

```
Thr Arg Tyr Ile Met Met Thr Ala Asn Gly Thr Leu Met Glu Ile Thr
            675                 680                 685

Ser Val Ile Ile Asp Ile Arg Gln Thr Ser Ile Phe Met Ile Met Leu
        690                 695                 700

Tyr Cys Ser Leu Gly Val Leu Leu Tyr Gly Leu Tyr Arg Leu Leu
705                 710                 715                 720

His Met Ile

<210> SEQ ID NO 11
<211> LENGTH: 258
<212> TYPE: PRT
<213> ORGANISM: Guinea pig cytomegalovirus
<220> FEATURE:
<223> OTHER INFORMATION: GP115

<400> SEQUENCE: 11

Met Tyr Glu Cys Met Phe Phe Ser His Arg Leu Thr Ile Gly Phe Tyr
1               5                   10                  15

Ile Pro Leu Ile Val Leu Thr Thr Met Ser Ser Leu Ser Glu Ser Leu
            20                  25                  30

Gly Glu Arg Gln Lys Thr Ala Cys Thr Val Ala Ala Ile Ser Cys Ala
        35                  40                  45

Asn Ser Asp Thr Tyr Asn Arg Thr Val Ser Asn His Thr Phe Phe
    50                  55                  60

Tyr Ile Ser Asp Arg Trp Lys Tyr Ser Glu Leu Ile Arg Tyr Glu Lys
65                  70                  75                  80

Pro Thr Gly Asp Leu Arg His Asp Lys Leu Ile His Val Asp Arg Glu
                85                  90                  95

Phe Leu Asp Ile Val Ser Leu Leu His Asn Asn Glu Asn Gln Leu Arg
            100                 105                 110

Thr Leu Leu Thr Ile Phe Arg Ser Asp Ser Ala Pro Pro Trp Val Lys
        115                 120                 125

Phe Met Arg Gly Tyr Ser Gln Cys Leu Asp His Pro Ile Ile Tyr Thr
    130                 135                 140

Cys Val Glu Glu Lys Cys Gln Gln Tyr Asn Leu Glu Glu Leu Pro Tyr
145                 150                 155                 160

Gly Lys Asp Ile Phe Leu Glu Asn Val Val Gly Phe Asp Leu Gly Ala
                165                 170                 175

Pro Pro His Asn Met Ser Val Leu Ile Ala Val Ser Asn Thr Lys Pro
            180                 185                 190

Lys Ile Thr Lys Val Leu Arg Ile Thr Ser Thr Ser Leu Thr Leu Phe
        195                 200                 205

Asp Ala Leu Tyr Asn Thr Val Leu Thr Phe Phe Arg Ser Ile Gly Ala
    210                 215                 220

Arg Asn Val Asp Val Val Arg Arg Leu Ile Leu Tyr Gln Ala Ser Leu
225                 230                 235                 240

Ser Gly Pro His Arg Asp Ala Pro Ile His Asn Tyr Leu Asn Arg Asp
                245                 250                 255

Leu Ser

<210> SEQ ID NO 12
<211> LENGTH: 179
<212> TYPE: PRT
<213> ORGANISM: Guinea pig cytomegalovirus
<220> FEATURE:
<223> OTHER INFORMATION: GP129
```

<400> SEQUENCE: 12

```
Met Arg Val Ile Val Leu Leu Val Met Phe Tyr Tyr Thr Arg Pro Gly
1               5                   10                  15

Ile Phe Asp Asp Pro Cys Cys Ile Tyr Ser Ser Lys Asp Arg Arg Val
                20                  25                  30

Gln His Ser Thr Thr Ser Asn Asp Thr Trp Arg Leu Val Arg Cys Gly
            35                  40                  45

Asn Thr Leu Met Val Ala Lys Arg Tyr Thr Asp Ser Phe Cys Glu Phe
        50                  55                  60

Ser Leu Glu Glu Asn Leu Phe Glu Ser Leu Ala Leu Asn Val Ser Arg
65                  70                  75                  80

Gln Glu Leu His Val Leu Ala Pro Glu Cys Lys Phe Gly Pro Val Glu
                85                  90                  95

Val Gly Ile Asn Lys Gln Val Arg Cys Ile Arg Tyr Pro Arg Met Pro
            100                 105                 110

Ser Val Gln Ser Lys Pro Glu Lys Pro Ser Ile Leu Gly Val Thr Tyr
        115                 120                 125

Arg Val Asp Tyr Thr Val Met Ile Pro Thr Pro His Phe Pro Arg Asp
130                 135                 140

Phe Asn Gly Leu Leu Cys Thr Phe Leu Glu Lys Asn Asp Thr Phe Tyr
145                 150                 155                 160

Asn Thr Thr Val Asp Val Cys Gly Ser Glu Phe Tyr Ser Val Asp Gly
                165                 170                 175

Asn Gly Lys
```

<210> SEQ ID NO 13
<211> LENGTH: 192
<212> TYPE: PRT
<213> ORGANISM: Guinea pig cytomegalovirus
<220> FEATURE:
<223> OTHER INFORMATION: GP131

<400> SEQUENCE: 13

```
Met Met Lys Arg Tyr Leu Val Leu Leu Pro Trp Ile Met Phe Tyr Ala
1               5                   10                  15

Ser Phe Gly Arg Ala Gly Arg Cys Tyr Tyr Pro Ser Thr Pro Ile Pro
                20                  25                  30

Lys Ser Phe Val Lys His Val Asp Thr Thr Arg Ser Leu Pro Glu Cys
            35                  40                  45

Glu Asn Asp Thr Val Ala Val Leu Thr Leu Thr Asn Gly Ala Lys Leu
        50                  55                  60

Tyr Val Asn Met Leu Asn Thr Trp Ile Asp Gly Tyr Ile Thr Thr Leu
65                  70                  75                  80

Gln Tyr Ala Ile Pro Pro Thr Leu Ser Asp Ile Phe Ala Phe Ile Lys
                85                  90                  95

Arg Arg Ile Asp Tyr Gly Ser Thr Gly Thr Ala Ala Ser Thr Leu Pro
            100                 105                 110

Ser Leu Thr Ser Leu Arg Thr Tyr Phe Gly Asp Arg Asp Ser Ser Phe
        115                 120                 125

Leu Trp His Tyr Thr Ile Arg Met Lys Asp Gly Ala Lys Thr Leu Asp
130                 135                 140

Cys Asp Val Tyr Val Thr Ser Arg Val His Phe Val Leu Asn Ser Tyr
145                 150                 155                 160

Glu Ala Val Gln Thr Val Leu Phe Glu Gly Gly Val Val Ile Ser Arg
                165                 170                 175
```

His Pro Ala Asp Ser Ile Ala Cys Leu Leu Ile Asn Trp Asn Trp Thr
            180                 185                 190

<210> SEQ ID NO 14
<211> LENGTH: 127
<212> TYPE: PRT
<213> ORGANISM: Guinea pig cytomegalovirus
<220> FEATURE:
<223> OTHER INFORMATION: GP133

<400> SEQUENCE: 14

Met Phe Trp Arg Leu Val Tyr Val Tyr Leu Val Ser Leu Leu Leu Ser
1               5                   10                  15

Ile Gly Ala Glu Asp Glu Gly Ile Asp Thr Trp Trp Leu Gly Gly Val
            20                  25                  30

Thr Asp Asn Thr Arg Val Lys Lys Glu Asn Gln Leu Ala His Tyr Ile
        35                  40                  45

Leu Lys Thr Ile Val Leu Thr His His Arg Arg Leu Arg Thr Gly Asp
    50                  55                  60

Glu Cys Thr Glu Gln Leu Ser Asn Asp Leu Asp Ile His Ser Val His
65                  70                  75                  80

Thr Leu Ala Asp Ser Ile Arg Arg Leu Arg Gly Arg Tyr Arg Lys Gly
                85                  90                  95

Leu Val Ser Ile Asp Gly Ile Arg Ile Ser Ile Gln Gln Ser Thr Arg
            100                 105                 110

Thr Gln Gln Lys Gly Leu Trp Ile Ser Ala Arg Ile Asp Arg Ala
        115                 120                 125

<210> SEQ ID NO 15
<211> LENGTH: 692
<212> TYPE: PRT
<213> ORGANISM: Guinea pig cytomegalovirus
<220> FEATURE:
<223> OTHER INFORMATION: GPCMV gB ectodomain

<400> SEQUENCE: 15

Met Arg Pro Val Arg Gly Ile Ala Arg Ser Arg Ile Leu Ser Cys Ser
1               5                   10                  15

Trp Arg Gly Thr Trp Thr Ser Ala Leu Thr Ile Leu Tyr Leu Gly Val
            20                  25                  30

Tyr Cys Glu Ser Thr Thr Val Thr Pro Thr Thr Val Glu Asp Thr Thr
        35                  40                  45

Val Ser Asn Gly Asn His Ser Asp Ala Ser Arg Asn Asn Thr Val Ile
    50                  55                  60

Arg Asn Leu Thr Ala Ser Val Asp Phe Ser Gln Arg Lys Leu Tyr Pro
65                  70                  75                  80

Tyr Arg Ile Cys Ser Met Ser Met Gly Thr Asp Leu Val Arg Phe Ala
                85                  90                  95

Arg Thr Ile Gln Cys Val Pro Phe Asn Pro Arg Val Asn Ser Glu Glu
            100                 105                 110

Gly Ile Met Leu Ile Tyr Lys Arg Asn Ile Leu Pro Tyr Val Phe Thr
        115                 120                 125

Ala Tyr Thr Tyr Gln Lys Glu Leu Leu Phe Gln Arg Ser Tyr Lys Gly
    130                 135                 140

His Arg Tyr Asp Tyr Leu Leu Gly Tyr Ser Arg Glu Phe Val Ala Leu
145                 150                 155                 160

Pro Met Trp Glu Ile Phe Leu Val Asn Ser Arg Gly Gln Cys Tyr Thr

```
                165                 170                 175
Ser His Gln Arg Val Ile Gly Ala Asp Arg Tyr Ile Ala Tyr His Asn
            180                 185                 190

Asp Asn Glu Val Asn Glu Thr Met Trp Leu Met Arg Asp Asp Met Gly
            195                 200                 205

Asn Asp Asp Thr Tyr Arg Tyr Ile Thr Val Lys Glu His Ala Arg Thr
            210                 215                 220

Pro Gly Ser Val Ala Phe His Lys Glu Thr Cys Ser Met Asn Cys Ile
225                 230                 235                 240

Val Thr Lys Thr Lys Gly Lys Ser Lys Phe Pro Tyr Asp Met Phe Val
                245                 250                 255

Leu Pro Ser Gly Val Ile Val Asn Ile Ser Pro Phe Tyr Asn Gly Ser
            260                 265                 270

Asn Gly Lys Thr Phe Arg Glu Gln Arg Glu Lys Phe His Ile Trp Ser
            275                 280                 285

Asn Tyr Ser Ile Leu Lys Asp Phe Gly Ser Arg Ala Leu Glu Ala Arg
            290                 295                 300

Ile Val Pro Lys Met Ala Phe Tyr Glu Arg Glu Asp Val Val Ile Gly
305                 310                 315                 320

Trp Glu Val Asn Asp Gln Ser Asn Val Thr Cys Glu Met Ile Leu Trp
                325                 330                 335

Glu Thr Val Asp Arg Ala Ile Arg Thr Glu Tyr Glu Asn Ala Phe His
            340                 345                 350

Tyr Val Ala Arg Thr Leu Thr Ser Thr Phe Val Glu Asn Lys Tyr Ser
            355                 360                 365

Pro Asp Asn Asn Leu Thr Glu Asp Ile Lys Cys Phe Lys Asn Asp
370                 375                 380

Ala Gln Lys Lys Ile Glu Glu Val Phe Leu Arg Asp Tyr Asn Glu Thr
385                 390                 395                 400

Tyr Asp Met Asp Gly Asn Ala Thr Tyr His Val Thr Thr Gly Gly Leu
                405                 410                 415

Val Ile Val Trp Gln Gly Leu Lys Gln Lys Ser Leu Lys Ala Leu Glu
            420                 425                 430

Ile Ala Ala Asn Glu Ser Ala Val Ser Ala Thr Gly Ser Asn Ser Arg
            435                 440                 445

Arg Lys Arg Ser Leu Pro Asp Glu Ser Thr Gly Asp Ile Ser Tyr Ala
450                 455                 460

Gln Leu Gln Phe Ala Tyr Asp Thr Leu Arg Thr Tyr Ile Asn Gln Ala
465                 470                 475                 480

Leu Gly His Ile Ala Glu Ala Trp Cys Leu Asp Gln Lys Arg Thr Ala
                485                 490                 495

Glu Val Leu His Glu Leu Ser Lys Ile Asn Pro Ser Asn Ile Leu Ser
            500                 505                 510

Ala Ile Phe Gly Val Pro Val Ala Ala Arg Val Val Gly Asp Val Ile
            515                 520                 525

Ser Leu Ala Lys Cys Ile Glu Val Asn Gln Ser Thr Val Leu Ile Lys
530                 535                 540

Gly Asp Met Arg Lys Phe Ser Asp Gly Lys Leu Glu Gly Cys Tyr
545                 550                 555                 560

Ser Arg Pro Val Val Trp Phe Ser Met Lys Asn Ser Thr Glu Val Arg
                565                 570                 575

Leu Gly Gln Leu Gly Glu Asp Asn Glu Ile Leu Leu Gly Thr His Arg
            580                 585                 590
```

```
Met Glu Thr Cys Gln Thr Gln Asp Tyr Arg Ile Phe Val Ala Gly Asp
            595                 600                 605

Ile Gly Tyr Glu Phe Gln Gln Tyr Val Phe Thr Lys Lys Ile Asn Leu
    610                 615                 620

Ser Glu Ile Asp Ile Ile Asp Thr Met Ile Ala Leu Lys Thr Glu Pro
625                 630                 635                 640

Leu Glu Asn Ile Asp Phe Lys Val Leu Glu Leu Tyr Ser Arg Asp Glu
                645                 650                 655

Leu Ala Gln Ala Asn Val Phe Asp Leu Glu Ser Ile Met Arg Glu Tyr
            660                 665                 670

Asn Tyr Gln Lys Lys Arg Leu Asp Phe Val Val Glu Arg Val Ile Asn
            675                 680                 685

Pro Ile Pro Pro
    690

<210> SEQ ID NO 16
<211> LENGTH: 698
<212> TYPE: PRT
<213> ORGANISM: Guinea pig cytomegalovirus
<220> FEATURE:
<223> OTHER INFORMATION: GP75 ectodomain

<400> SEQUENCE: 16

Met Ser Pro Ala Thr Arg Phe Thr Val Ile Ser Cys Leu Val Val Ser
1               5                   10                  15

Leu Ile Thr Pro Ser Glu Thr Ser Ser Trp Phe Asp Pro Phe Ile Glu
            20                  25                  30

Trp Ala Arg Ser Ser Pro Asn Met Thr Cys Val Asn Asn Arg Thr Gly
        35                  40                  45

Thr Arg Ser Leu Ala Thr Glu Gly Leu Ile Ser Phe Asn Phe Tyr Glu
    50                  55                  60

Ala Ser Arg Thr Val Arg Thr Tyr Gln Val Pro Lys Cys Ile Phe Met
65                  70                  75                  80

Ser Ser Val Ser Lys Thr Ile Met Gln Gly Val Asp Leu Phe Glu Ser
                85                  90                  95

Leu Glu Ser Tyr Arg Arg Arg Tyr Tyr Ser Tyr Ile Ile Val Pro Val
            100                 105                 110

His Ala Ser Phe Gln Ile Phe Ile His Asp Leu Arg Thr Asp Leu Ser
        115                 120                 125

Ser Pro Thr Glu Glu Leu Thr Ser Pro Val Asp Lys Thr Leu Pro Asn
    130                 135                 140

Val Thr Ile Trp His Thr Pro Ser Gly Tyr Val Ile Arg Leu Leu Asp
145                 150                 155                 160

Val Val Thr Pro Arg Phe Glu Glu Cys Thr Leu Phe Pro Asn His Thr
                165                 170                 175

Val Ile Phe Asp Met Thr Val Pro Cys Ser Gln Glu Val Tyr Leu Arg
            180                 185                 190

Gln Thr Gly Lys His Gln Phe Ala Ile Val Leu Thr Phe Thr Pro Ser
        195                 200                 205

Phe Phe Val Leu Asn Ile Gln Thr Ala Gln His Gln His Val Thr Glu
    210                 215                 220

Asn Asp Glu Asp Val Ile Leu Ile Phe Gly Asp Val Arg Ser Ile Asp
225                 230                 235                 240

Val Lys Ala Pro Tyr Ser Lys Pro Val Leu Thr Leu Arg Gln Ser Tyr
                245                 250                 255
```

```
Arg Asp Asp Leu Leu Ile Val Ala Lys Thr Ser Ile Val Asn Ala Thr
        260                 265                 270

Tyr Pro Phe Ile Lys Thr Gln Asp Phe Leu Lys Gly Thr Leu Ser Gly
        275                 280                 285

Asn Tyr Leu Asp Phe Asn His Val Tyr Thr Glu Phe Asn Arg Leu Val
        290                 295                 300

Ile His Asn Leu Val Glu Gly Leu Cys Asp Ala Pro Pro Asp Asp Arg
305                 310                 315                 320

Thr Val Ser Met Val Phe Ser Tyr Ala Val Leu Ala Arg Thr Leu Tyr
                325                 330                 335

His Thr Ser Asn Val Thr Ala Arg Leu Glu Asp Val Ala Leu Arg Tyr
            340                 345                 350

Val Arg Leu Thr Leu Ala Arg Thr Phe Leu Gln Gln Cys Phe Asp Val
        355                 360                 365

Gly Pro Arg Tyr Met Arg Phe Pro Thr Ile Asp Gly Ala Leu Ser Val
        370                 375                 380

Leu Leu Lys Leu Ile Arg Asn Ser Arg Asp Val Asp Gly Gly Leu Lys
385                 390                 395                 400

Leu Ser Leu Thr Phe Ala Leu Ile Phe Gly Asn Asn Thr Asp Met Thr
                405                 410                 415

Lys Glu Arg Asp Leu Glu Asn Ala Leu Tyr Glu Met Lys Ser Ile His
            420                 425                 430

Arg Ala Gly Leu Val Ser Pro Leu Ser Pro Arg Gln Arg Ser Leu Leu
        435                 440                 445

Tyr Met Met Ala Tyr Val Thr His His Thr Thr Ala Phe Pro Asp Ile
        450                 455                 460

Arg Arg Glu Met Leu Ala Met Gln Thr Ser Leu Cys Ser Pro Gln Glu
465                 470                 475                 480

Leu Tyr Asn Trp Ala Pro His Val Ser Ser Ala Gly Leu Thr Met Gln
                485                 490                 495

Glu Met Phe Thr Pro Cys Ser Gly Ser Gly Arg Arg Asp Tyr Ser Glu
            500                 505                 510

Ala Arg Ile Ala Glu Ile Val Gln Leu Asn Pro Leu Thr Thr Lys Thr
        515                 520                 525

Pro Ala Asp Leu Tyr Arg Ile Leu Ala His Phe Asp Arg Ser Asn Leu
        530                 535                 540

Thr Asn Phe Pro Ala Leu Ser Cys Ile Ser His Leu Ser Gly Tyr Val
545                 550                 555                 560

Ala Val Thr Leu Arg Asp Val Thr Tyr Val Val Ser Ser Asn Val Met
                565                 570                 575

Leu Lys Gly Thr Ser Tyr Pro Val Thr Asn Leu Ala Val Asp Lys Thr
            580                 585                 590

Met Ile Val Thr Val Ser Pro Ala Gln His Pro Cys Glu Lys Thr Glu
        595                 600                 605

Val Ala His Ala Thr Arg Ser Ile Pro Ile Val Lys Asn Ile Thr Ile
        610                 615                 620

Gly Asn Asp Cys Glu Tyr Cys Lys Ser Ala Ile Met Glu Tyr Asp Glu
625                 630                 635                 640

Val Asn Gly Leu Ser Asn Ile Val Tyr Leu Ala Asp Thr Ala Asp Leu
                645                 650                 655

Val Leu Val Thr Asn Leu Asp Asn Arg Ile Leu Ala Ser Ser Pro Arg
            660                 665                 670
```

Thr Arg Tyr Ile Met Met Thr Ala Asn Gly Thr Leu Met Glu Ile Thr
    675                 680                 685

Ser Val Ile Ile Asp Ile Arg Gln Thr Ser
    690                 695

<210> SEQ ID NO 17
<211> LENGTH: 22
<212> TYPE: DNA
<213> ORGANISM: Artificial Sequence
<220> FEATURE:
<223> OTHER INFORMATION: GPCMV GP83 Forward Primer

<400> SEQUENCE: 17
cgacgacgac gatgacgaaa ac                                               22

<210> SEQ ID NO 18
<211> LENGTH: 22
<212> TYPE: DNA
<213> ORGANISM: Artificial Sequence
<220> FEATURE:
<223> OTHER INFORMATION: GPCMV GP83 Reverse Primer

<400> SEQUENCE: 18
tcctcggtct caacgaaggg tc                                               22

<210> SEQ ID NO 19
<211> LENGTH: 17
<212> TYPE: DNA
<213> ORGANISM: Artificial Sequence
<220> FEATURE:
<223> OTHER INFORMATION: GPCMV GP83 FAM Probe

<400> SEQUENCE: 19
atccgagtta ggcagcg                                                     17

<210> SEQ ID NO 20
<211> LENGTH: 17
<212> TYPE: DNA
<213> ORGANISM: Artificial Sequence
<220> FEATURE:
<223> OTHER INFORMATION: Guinea pigs B-actin Forward Primer

<400> SEQUENCE: 20
tggatcggcg gctcatc                                                     17

<210> SEQ ID NO 21
<211> LENGTH: 22
<212> TYPE: DNA
<213> ORGANISM: Artificial Sequence
<220> FEATURE:
<223> OTHER INFORMATION: Guinea pigs B-actin Reverse Primer

<400> SEQUENCE: 21
catcgtactc ctgcttgctg at                                               22

<210> SEQ ID NO 22
<211> LENGTH: 15
<212> TYPE: DNA
<213> ORGANISM: Artificial Sequence
<220> FEATURE:
<223> OTHER INFORMATION: Guinea pigs B-actin Prober

<400> SEQUENCE: 22
cactctccac cttcc                                                       15

VACCINE FOR PREVENTING OR TREATING CONGENITAL INFECTION WITH CYTOMEGALOVIRUS

RELATED PATENT APPLICATIONS

This application is based on and claims the benefit of priority from International Application No. PCT/JP2019/047966, filed on Dec. 6, 2019, which claims priority to Japanese Patent Application No. 2018-230640, filed on Dec. 10, 2018, the contents of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on May 23, 2021, is named "FP19-1095-00_Amended_Sequence_Listing.txt" and is 66.5 KB in size.

TECHNICAL FIELD

The present invention relates to a vaccine for preventing or treating congenital infection with cytomegalovirus.

BACKGROUND ART

Cytomegalovirus (CMV) infections include major two. The first is congenital CMV infections, which develop in a fetus when a pregnant woman is infected for the first time and the second one is organ dysfunctions such as CMV pneumonia, enteritis, and retinitis, which develop in patients in immunocompromised states such as transplantation, AIDS, and congenital immunodeficiency. Of these, the congenital CMV infection is one of the TORCH syndrome and an important congenital infection that causes malformation or severe clinical manifestations in fetuses. When pregnant women are infected with CMV for the first time, the congenital infection occurs in approximately 40% of the fetuses via the placenta (as used herein, the term "congenital infection" and the term "transplacental infection" are used in the same meaning) Moreover, there is a report that approximately 15% of stillbirths are due to congenital CMV infection. The annual number of occurrences of infants with congenital infection is 3000 or more in Japan and approximately 40000 in the United States, and symptomatic ones are said to be approximately 1000 in Japan and approximately 8000 in the United States, of which postinfectious disorders, such as central nerve disorders and hearing loss persist in approximately 90% of them.

The CMV seropositive rate in Japan is higher than those in North American and European countries, 80% to 90% of Japanese adults are CMV seropositive and most people are infected in infancy. However, the CMV seropositive rate in young people has shown a decreasing tendency from the 90-100% range to the 60-70% range, as a recent tendency, and the need of prophylaxis against congenital CMV infection has further increased (Non Patent Literature 1).

The Institute of Medicine in the United States has made an analysis that congenital CMV infection has an impact exceeding Down syndrome as a cause of congenital central nerve disorders in developed countries and CMV vaccines are classified in the category with the highest medical economic cost-effectiveness on the basis of the calculation of decrease in lifetime QOL for infants with congenital infection who had lasting disorders and socioeconomic loss as QALYs (Quality-adjusted life years) (Non Patent Literature 2).

Pathogens that cause infection are classified roughly into Class I pathogens, of which conventional vaccines can yield sufficient effects, and Class II pathogens, of which sufficient protective immunity cannot be acquired by conventional vaccines or history of infection with the pathogen, and CMV is classified in the latter. It is indicated to be a reason for the difficulty of conquest over Class II pathogens that they have sophisticated mechanisms of escaping the immunity. Humankind has so far developed many effective vaccines against Class I pathogens and defeated the menace of infections that they cause. The focus of future vaccine development is moving to Class II pathogens.

To minimize the damage of congenital CMV infection, identification of uninfected pregnant women by screening of pregnant women and enlightenment of such women on measures to take in daily life are conducted, but they are not enough. Furthermore, although there is a report claiming that it was effective for prevention of infection and reduction of aggravation in fetuses to identify pregnant women with infection for the first time and administer an anti-CMV hyperimmunoglobulin to the pregnant women, its efficacy is currently being questioned (Non Patent Literature 3). Meanwhile, ganciclovir has also been marketed as a small molecule drug, but its effect is limited and there are problems of side effects. Since currently a CMV vaccine does not exist, and there is no therapy effective enough as described above, it is considered that its unmet needs are high.

About CMV vaccine development, studies using attenuated live vaccines, subunit vaccines, DNA vaccines, and the like have so far been attempted in a plurality of pharmaceutical companies and academia, but both T-cell immune and B-cell immune responses are insufficient with any of such vaccines and, as a result, an effect that is worthy of practical use as a vaccine has been not gained.

Among them, the vaccine from Sanofi S. A., which is a subunit vaccine containing the CMV glycoprotein gB as an antigen, exhibited an infection-preventing effect of approximately 50% in a clinical trial targeted to uninfected adult women. While the development was practically stopped because the effect was limited, a significant finding that "a gB antigen alone can exhibit a certain (but not sufficient) effect" was obtained (Non Patent Literature 4).

For the experimental proof for the effect of CMV vaccine candidate products, it is necessary to consider the species specificity of CMV. Because CMV has species specificity, animal experiments using human cytomegalovirus (HCMV) is basically impossible. Animal experiments, which are performed using mice, rats, guinea pigs, monkeys, or the like, are carried out using CMVs specific to various animal species. For transplacental infection, only guinea pig is an animal model system in which infection to fetuses can be confirmed by causing viral infection to mothers without any special treatment and the guinea pig test system of transplacental infection is used widely (Non Patent Literature 5).

About the effect of gB vaccines on transplacental infection, it has been reported that first infections of female guinea pigs were suppressed and transplacental infections to fetuses were also suppressed by administration to female guinea pigs of a recombinant GPCMV gB protein+adjuvant (Non Patent Literature 6).

In Non Patent Literature 7, it is described that using an adenoviral vector vaccine in which a GPCMV gB protein is incorporated, gB suppresses transplacental infection to a fetus in a guinea pig model of transplacental infection.

Meanwhile, pentamer antigens have attracted considerable attention as main antigens of CMV in these several years. The pentamer is a cell-tropism determinant of CMV and a molecule composed of the five subunits gH, gL, UL128, UL130, and UL131 (gH/gL/UL128/UL130/UL131) in human CMV.

About the contribution of the pentamer to the transplacental infection, it has been reported that GPCMV in which pentamer genes are deleted lacks the infectivity to epithelial and endothelial cells, and they revive by expressing the deleted genes ectopically (Non Patent Literature 8).

Moreover, about the effect of pentamer vaccines, it has been reported that in the results of detailed analysis about monoclonal antibodies induced by administering to mice the vector vaccine MVA-PC in which the pentamer is expressed, the neutralizing ability of anti-pentamer antibodies in epithelial and endothelial cell lines was clearly higher than that of anti-gH antibodies, and for the neutralizing ability in trophoblastic cells, which are considered to be important in transplacental infection, was also similar (Non Patent Literature 9).

On the other hand, there are also contradicting reports. In Non Patent Literature 10, it is described that trophoblast progenitor cells in the placenta of humans are a target of CMV and contribution of the pentamer to infection of the cells with CMV was hardly found, but contribution of gB was clearly found.

Moreover, in Non Patent Literature 11, it is described that contribution of the pentamer to infection to placenta tissue and proliferation of GPCMV was hardly found using an ex vivo test system of placenta infection.

As seen above, while reports suggesting the usefulness of the pentamer as a vaccine antigen are found here and there, the role of the pentamer in transplacental infection is not clear and it is in a situation where it cannot yet be said that a conclusion is made about the suppressive effect of pentamer vaccines on transplacental infection.

About the effect of combined application of the pentamer and gB, in Patent Literature 1, it is reported that combined application of the pentamer and gB was effective in infection protection test using monkeys as subjects, but no suggestion is provided about the influence on transplacental infection. Moreover, while it has been indicated that the combined application group of pentamer+gB is superior in comparison with the pentamer single administration group and the non-immunization group, to be precise, it is not considered as an indication of the effect of combined application since no gB single administration group has been set.

Moreover, in Non Patent Literature 12, while it is described that there is an advantage in the combined application for neutralizing ability and suppression of emergence of resistant strains on the basis of in vitro verification of combined effect of an anti-gB monoclonal antibody and an anti-pentamer monoclonal antibody, the effect of combined application for the protective ability against infection in the living body is not proved.

Furthermore, in Patent Literature 2, there is data that production of some cytokines is higher by immunization with a gB+pentamer bivalent vaccine than that in the single administration groups, but the combined application group is not superior in the neutralizing ability and no infection experiment is conducted.

CITATION LIST

Patent Literature

Patent Literature 1: International Publication No. WO 2017153954
Patent Literature 2: Japanese Unexamined Patent Publication No. 2017-515503
Patent Literature 3: International Publication No. WO 2003004647

Non Patent Literature

Non Patent Literature 1: Azuma H et al., "Cytomegalovirus seropositivity in pregnant women in Japan during 1996-2009" J Jpn Soc Perin Neon Med 46 (2010) 1273-1279
Non Patent Literature 2: Kathleen R. Stratton et al., "Vaccines for the 21st century: a Tool for Decisionmaking" The National Academies Press, 2000
Non Patent Literature 3: Revello M G et al., "Randomized trial of hyperimmune globulin to prevent congenital cytomegalovirus" N Engl J Med 370 (2014) 1316-1326
Non Patent Literature 4: Rieder F et al., "Cytomegalovirus vaccine: phase II clinical trial results" Clin Microbiol Infect 20 Suppl 5 (2014) 95-102
Non Patent Literature 5: Yamada S et al., "Characterization of the guinea pig cytomegalovirus genome locus that encodes homologs of human cytomegalovirus major immediate-early genes, UL128, and UL130" Virology 391 (2009) 99-106
Non Patent Literature 6: Schleiss M R et al., "Glycoprotein B(gB) vaccines adjuvanted with AS01 or AS02 protect female guinea pigs against cytomegalovirus (CMV) viremia and offspring mortality in a CMV-challenge model" Vaccine 32 (2014) 2756-2762
Non Patent Literature 7: Hashimoto K et al., "Effects of immunization of pregnant guinea pigs with guinea pig cytomegalovirus glycoprotein B on viral spread in the placenta" Vaccine 31 (2013) 3199-3205
Non Patent Literature 8: Coleman S et al., "A Homolog Pentameric Complex Dictates Viral Epithelial Tropism, Pathogenicity and Congenital Infection Rate in Guinea Pig Cytomegalovirus" PLoS Pathog 12 (2016) e1005755
Non Patent Literature 9: Flavia Chiuppesi et al., "Vaccine-Derived Neutralizing Antibodies to the Human Cytomegalovirus gH/gL Pentamer Potently Block Primary Cytotrophoblast Infection" J Virol 89 (2015) 11884-11898
Non Patent Literature 10: Martin Zydek et al., "HCMV Infection of Human Trophoblast Progenitor Cells of the Placenta Is Neutralized by a Human Monoclonal Antibody to Glycoprotein B and Not by Antibodies to the Pentamer Complex" Viruses 6 (2014) 1346-1364
Non Patent Literature 11: Yamada S et al., "An Ex vivo culture model for placental cytomegalovirus infection using slices of Guinea pig placental tissue" Placenta 37 (2016) 85-88
Non Patent Literature 12: Patel H D et al., "In Vitro Characterization of Human Cytomegalovirus-Targeting Therapeutic Monoclonal Antibodies LJP538 and LJP539" Antimicrob Agents Chemother 60 (2016) 4961-4971
Non Patent Literature 13: Burke H G et al., "Crystal Structure of the Human Cytomegalovirus Glycoprotein B" PLoS Pathog 11 (2015) e1005227
Non Patent Literature 14: Ciferri C et al., "Structural and biochemical studies of HCMV gH/gL/gO and Pentamer reveal mutually exclusive cell entry complexes" Proc Natl Acad Sci USA 112 (2015) 1767-1772

Non Patent Literature 15: Kanai K et al., "Re-evaluation of the genome sequence of guinea pig cytomegalovirus" J Gen Virol 92(Pt 5) (2011) 1005-1020

Non Patent Literature 16: Yamada S et al., "Guinea pig cytomegalovirus GP129/131/133, homologues of human cytomegalovirus UL128/130/131A, are necessary for infection of monocytes and macrophages" J Gen Virol 95(Pt 6) (2014) 1376-1382

SUMMARY OF INVENTION

Technical Problem

As described above, a CMV vaccine effective in prevention of infection with CMV, in particular, capable of suppressing congenital infection with CMV, does not exist. Therefore, the present invention is directed to provide an effective vaccine capable of preventing and treating congenital infection with CMV.

Solution to Problem

The present inventors have found that congenital CMV infection in guinea pigs can be strongly suppressed by using gB and pentamer together, which are main antigens of CMV, to prepare a bivalent vaccine, thereby completing the present invention.

Accordingly, the present invention relates to each of the following inventions.

[1] A vaccine for preventing or treating congenital infection with cytomegalovirus (CMV), comprising a CMV envelope glycoprotein B (gB protein) antigen and a pentamer antigen.

[2] The vaccine according to [1], wherein the gB protein antigen is an ectodomain of a CMV gB protein.

[3] The vaccine according to [2], wherein the gB protein antigen is an ectodomain of a human cytomegalovirus (HCMV) gB protein having the amino acid sequence set forth in SEQ ID NO: 1.

[4] The vaccine according to any one of [1] to [3], wherein the pentamer antigen consists of human cytomegalovirus (HCMV) gH, gL, UL128, UL130, and UL131.

[5] The vaccine according to [4], wherein the pentamer antigen is ectodomains of human cytomegalovirus (HCMV) pentamer proteins having the amino acid sequences set forth in SEQ ID NO: 2, SEQ ID NO: 3, SEQ ID NO: 4, SEQ ID NO: 5, and SEQ ID NO: 6.

[6] A vaccine kit for preventing or treating congenital infection of human cytomegalovirus (HCMV), comprising:
a vaccine comprising an HCMV envelope glycoprotein B (gB protein) antigen; and
a vaccine comprising a pentamer antigen consisting of HCMV gH, gL, UL128, UL130, and UL131.

[7] Use of a human cytomegalovirus (HCMV) envelope glycoprotein B (gB protein) antigen and a pentamer antigen consisting of HCMV gH, gL, UL128, UL130, and UL131, in manufacture of a vaccine or a vaccine kit for preventing or treating congenital infection with HCMV.

Advantageous Effects of Invention

According to the present invention, it is possible to provide, by using a gB protein antigen and a pentamer antigen together, a vaccine having an infection-suppressing effect exceeding the effect of single administration of each, in protection against congenital infection with CMV. In this way, practical application of CMV vaccines can be anticipated.

BRIEF DESCRIPTION OF DRAWINGS

FIG. 9 illustrates a result of evaluation of GPCMV-gB binding antibody titer contained in immune serum for GPCMV-gB or GPCMV-Pentamer or two of GPCMV-gB and GPCMV-Pentamer.

FIG. 10 illustrates a result of evaluation of GPCMV-Pentamer binding antibody titer contained in an immune serum for GPCMV-gB or GPCMV-Pentamer or two of GPCMV-gB and GPCMV-Pentamer.

FIG. 11 illustrates a result of evaluation of HCMV-gB binding antibody titer contained in an immune serum for HCMV-gB or HCMV-Pentamer or two of HCMV-gB and HCMV-Pentamer.

FIG. 12 illustrates a result of evaluation of HCMV-Pentamer binding antibody titer contained in an immune serum for HCMV-gB or HCMV-Pentamer or two of HCMV-gB and HCMV-Pentamer.

DESCRIPTION OF EMBODIMENTS

Figure 1:
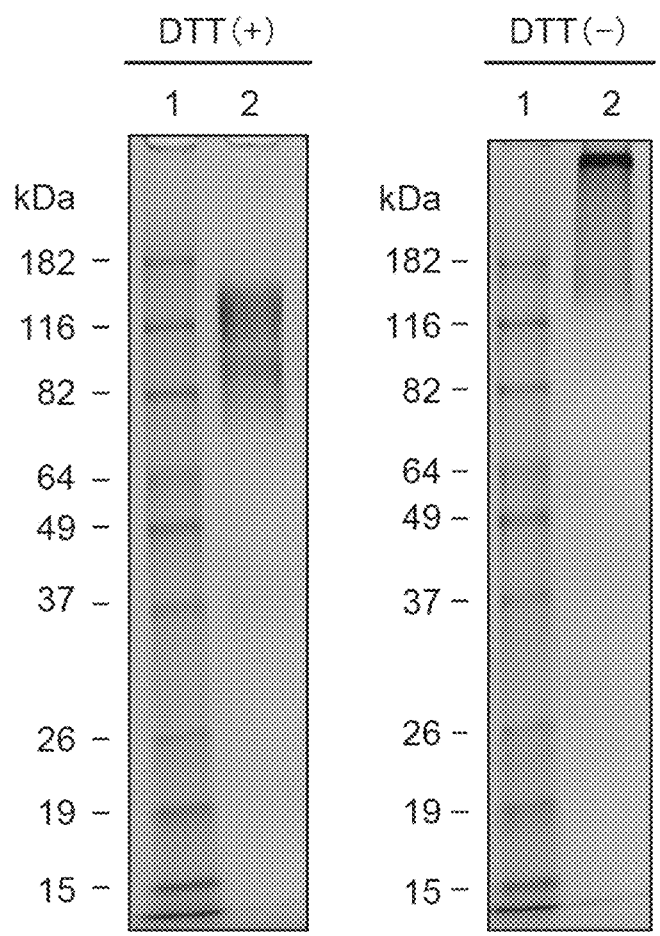
FIG. 1 illustrates a result of characteristic analysis of GPCMV-gB by SDS-PAGE.

One embodiment of the vaccine according to the present invention is a vaccine for preventing or treating congenital infection with cytomegalovirus (CMV), comprising a CMV envelope glycoprotein B (gB protein) antigen and a pentamer antigen. That is, the vaccine according to this embodiment is a bivalent vaccine containing two kinds of antigen proteins.

The cytomegalovirus (CMV) includes any CMV strain and examples thereof include human cytomegalovirus (HCMV), guinea pig cytomegalovirus (GPCMV), murine cytomegalovirus (MCMV), rat cytomegalovirus (RCMV), and rhesus cytomegalovirus (RhCMV).

The CMV gB protein may be a wild type CMV gB protein or a modified type CMV gB protein.

The "wild type CMV gB protein" means a gB protein derived from any CMV strain and examples thereof include a gB protein (GenBank ACCESSION No.: X17403.1) derived from the strain HCMV AD169 having the amino acid sequence set forth in SEQ ID NO: 7 and a gB protein (GenBank accession No.: AB592928.1) derived from the GPCMV strain 22122 having the amino acid sequence set forth in SEQ ID NO: 8.

Examples of the modified type CMV gB protein include a variant having a modification for preventing the formation of aggregates, a variant having a modification for improving antibody inducing ability or neutralizing antibody inducing ability, and the like. The "neutralizing antibody inducing ability" refers to ability capable of inducing neutralizing antibodies to an antigen protein, which can be evaluated with the neutralizing antibody titer in immune serum obtained by inoculating the antigen protein into a test animal. The "neutralizing antibody" refers to an antibody capable of eliminating the infectivity of virions and the level of the neutralizing activity of the antibody can be evaluated with the concentration (NT50) of the antibody necessary to decrease, for example, 50% of the number of plaques of the test virus.

The modified type CMV gB proteins refers to proteins modified from the wild type CMV gB by substitution, deletion, or addition of at least one amino acid residue or region of consecutive amino acid residues and also include proteins with a protein modification not found in wild type proteins, such as proteins with sugar chain introduction by substitution or deletion of an amino acid residue.

The CMV gB protein antigen may be the full length of a gB protein or a partial fragment of the gB protein. Examples of the fragment include an ectodomain or a partial region of an ectodomain of a CMV gB protein. Examples of the full length of a gB protein include an HCMV gB protein having the amino acid sequence set forth in SEQ ID NO: 7 (GenBank ACCESSION No.: X17403.1). However, in the amino acid sequence set forth in SEQ ID NO: 7, an amino acid sequence of amino acids from positions 1 to 24 is a leader sequence. Examples of the ectodomain include an HCMV gB protein fragment having an amino acid sequence of amino acids from positions 25 to 706 in the amino acid sequence set forth in SEQ ID NO: 7.

Moreover, these gB protein antigens may be those with characteristics improved by amino acid substitution or the like. Examples thereof include an HCMV gB protein ectodomain variant (SEQ ID NO: 1) modified from an HCMV gB protein ectodomain having an amino acid sequence of amino acids from positions 1 to 706 in the amino acid sequence set forth in SEQ ID NO: 7, in reference to Non Patent Literature 13, by substitution of the amino acid residue at position 156 with a histidine residue (His), the amino acid residue at position 157 with an arginine residue (Arg), the amino acid residue at position 239 with a glutamic acid residue (Glu), the amino acid residue at position 240 with an alanine residue (Ala), the amino acid residue at position 456 with a threonine residue (Thr), and the amino acid residue at position 458 with a glutamine residue (Gln).

The CMV gB protein antigen may be prepared by protein purification using CMV and can be prepared by a genetic engineering technique. The method of preparation is not particularly limited, but the CMV gB protein antigen may be obtained, for example, by obtaining a nucleic acid by PCR using a cDNA of a wild type gB protein as a template and designing a primer, operatively linking the nucleic acid to an expression promoter, optionally further linking a tag, introducing the nucleic acid into an appropriate expression vector, and expressing the nucleic acid. The prepared CMV gB protein antigen may be purified as needed. The method of purification is not particularly limited, but examples thereof include purification with an affinity chromatography column, or the like.

When the modified type gB protein antigen is a variant by introduction of a mutation, the modified type gB protein antigen may be obtained by designing a primer for introducing a mutation of interest, obtaining a nucleic acid having mutation introduced by PCR, operatively linking the nucleic acid to an expression promoter, optionally further linking a tag, introducing the nucleic acid into an appropriate expression vector, and expressing the nucleic acid.

Moreover, when a modified type gB protein antigen is a variant by sugar chain introduction (glycosylation), the method of sugar chain introduction may be a conventional method and is not particularly limited, but, for example, when an N-sugar chain is introduced, a cDNA of the wild type gB protein is used as a template, primers are designed such that 3 consecutive amino acid sequences at the target site to introduce the N-linked sugar chain are N-X-S/T (X is any amino acid other than proline), and a mutation is introduced by PCR. A modified type CMV gB protein can be obtained by cloning a nucleic acid sequence for the modified gB protein of interest or the nucleic acid sequence further linked to a tag such as 6×His, as needed, into an appropriate vector and expressing the nucleic acid. Then, an N-sugar chain is added to asparagine of the target site of the gB variant by a conventional method.

The CMV pentamer is also referred to as a pentameric complex or simply a pentamer. The CMV pentamer may be a wild type CMV pentamer or a modified type CMV pentamer.

The wild type CMV pentamer means a pentamer derived from any CMV strain and examples thereof include a pentamer consisting of human cytomegalovirus (HCMV) gH, gL, UL128, UL130, and UL131, a pentamer consisting of guinea pig cytomegalovirus (GPCMV) GP75 (gH), GP115 (gL), GP129 (UL128), GP131 (UL130), and GP133 (UL131), and the like.

Examples of the HCMV pentamer include pentamer proteins (GenBank ACCESSION No.: AY446894.2) derived from a HCMV strain Merlin having the amino acid sequences set forth in SEQ ID NO: 2 (gH), SEQ ID NO: 3 (gL), SEQ ID NO: 4 (UL128), SEQ ID NO: 5 (UL130), and SEQ ID NO: 6 (UL131) (in addition, alteration has been made based on the sequence information of other CMV strains since the nucleotide sequence of UL128 contains mutations) and the like.

Examples of the GPCMV pentamer include pentamer proteins (GenBank ACCESSION No.: AB592928.1) derived from the GPCMV strain 22122 having the amino acid sequences set forth in SEQ ID NO: 10 (GP75), SEQ ID NO: 11 (GP115), SEQ ID NO: 12 (GP129), SEQ ID NO: 13 (GP131), and SEQ ID NO: 14 (GP133) (in addition, alteration has been made based on the sequence information of other CMV strains since the nucleotide sequence of GP133 contains mutations) and the like.

Examples of the modified type CMV pentamer include a variant having a modification for preventing the formation of aggregates, a variant having a modification for improving antibody inducing ability or neutralizing antibody inducing ability, and the like. The modified type CMV pentamer refers to a pentamer in which at least one of the five proteins composing a wild type CMV pentamer is a modified protein and refers to a protein modified from a wild type CMV pentamer by substitution, deletion, or addition of at least one amino acid residue or region of consecutive amino acid residues and also includes proteins with a protein modification not found in wild type proteins, such as proteins with sugar chain introduction by substitution or deletion of an amino acid residue.

The CMV pentamer antigen may be prepared by protein purification using CMV and can be prepared by a genetic engineering technique. The method of preparation is not particularly limited, but, the CMV pentamer antigen may be obtained, for example, by obtaining a nucleic acid by PCR using cDNAs of five proteins composing a wild type pentamer as templates and designing a primer, operatively linking the nucleic acids to expression promoters, optionally further linking a tag, introducing the nucleic acids into an appropriate expression vector, expressing the nucleic acids, and folding to form a pentamer structure. The CMV pentamer antigen can be expressed as a secreted type protein, as needed. Expression as a secreted type protein is made possible, for example, by expressing gH not full length (SEQ ID NO: 9), but as a fragment of the ectodomain (SEQ ID NO: 2). The prepared CMV pentamer antigen may be purified, as needed. The method of purification is not particularly limited, but examples thereof include purification with an affinity chromatography column, or the like.

When the modified type CMV pentamer antigen is a variant by introduction of a mutation or a variant by sugar chain introduction (glycosylation), it can be prepared as described above.

The vaccine according to this embodiment may contain a CMV gB protein antigen and a CMV pentamer antigen, for example, at a mass ratio of from 1:10 to 10:1 and it is preferable that it is contained in the same mass. As the content of protein antigens in the vaccine, the CMV gB protein antigen and the CMV pentamer antigen may each be 0.1-1000 µg and it is preferable that each is 1-100 µg.

The dosage form of the vaccine according to this embodiment may be, for example, liquid form, powdered form (freeze-dried powder, dry powder), capsules, tablet form, or frozen state.

The CMV vaccine according to this embodiment may comprise a pharmaceutically acceptable carrier. As the above-described carrier, a carrier that is usually used for vaccine manufacture may be used without limitation and, specifically, examples include saline, buffered saline, dextrose, water, glycerol, aqueous isotonic buffer solutions, and combinations thereof. The vaccine may further contain an emulsifier, a preservative (for example, thimerosal), a tonicity adjusting agent, a pH adjuster, an inactivated agent (for example, formalin), or the like, as appropriate.

To further increase immunogenicity of the vaccine according to this embodiment, an adjuvant may further be contained. Examples of the adjuvant include oil-in-water type emulsion adjuvants (AS03, MF59, and the like) such as aluminum adjuvants or squalene, ligands of Toll-like receptors such as CpG and 3-O-deacyl-4'-monophosphoryl lipid A (MPL), polymer adjuvants such as saponin adjuvants, poly-γ-glutamic acid, and polysaccharides such as chitosan and inulin.

The vaccine according to this embodiment can be obtained by mixing the CMV gB protein antigen and a CMV pentamer antigen, and a carrier, an adjuvant, or the like, as needed. The adjuvant may be an adjuvant that is mixed at the time of use.

The administration route of the vaccine according to this embodiment may be, for example, transdermal administration, sublingual administration, ophthalmic administration, intradermal administration, intramuscular administration, oral administration, enteral administration, transnasal administration, intravenous administration, subcutaneous administration, intraperitoneal administration, or inhalational administration from mouth to lung.

The mode of administration of the vaccine according to this embodiment may be, for example, a mode of administration with a syringe, a transdermal patch, microneedles, an implantable sustained release device, a syringe with microneedles, a needle-free device, or spray.

According to the vaccine according to this embodiment, transplacental infection with CMV can be prevented or treated. The prevention of transplacental infection is to suppress vertical transmission of CMV to a fetus by administering a vaccine to a mother or to suppress expression of various symptoms caused by congenital infection. These can be evaluated by examination by nucleic acid amplification method using the amniotic fluid of fetuses or the body fluid of newborn infants, head sonography examination, head CT examination, head MRI examination, or hearing screening of newborn infants, or the like. The treatment of transplacental infection is to suppress expression and progression of various symptoms caused by congenital infection by administering the vaccine to infants with congenital infection. These can be evaluated by audiometry tests, visual acuity tests, other physical examinations or mental developmental examinations, or the like of infants with congenital infection. It is preferable that the vaccine according to this embodiment is administered to women at a baby bearing age or girl children as subjects. From the viewpoint of herd immunity, men, boy children, and elderly people being included as subjects may also be taken into consideration. Moreover, it is desirable that the number of administrations is once to three times, provided that the vaccine is inoculated a plurality of times at 2-month to several-year intervals. It is also possible to measure the blood antibody titer and select people who are negative for antibody or of a low antibody titer as subjects to be inoculated.

The vaccine kit according to the present invention is a vaccine kit for preventing or treating transplacental infection with HCMV, comprising a vaccine comprising an HCMV gB protein antigen and a vaccine comprising a pentamer antigen consisting of HCMV gH, gL, UL128, UL130, and UL131. That is, it is a vaccine kit comprising two kinds of vaccines of a univalent vaccine comprising an HCMV gB protein antigen and a univalent vaccine comprising an HCMV pentamer antigen.

The two kinds of vaccines may be administered after mixing or administered separately. When administered separately, they may be administered sequentially, in any order, and, for example, within 15 minutes after administration of the first kind, the second kind is administered.

EXAMPLES

[Materials and Method]
<Preparation of GPCMV-gB and Characteristic Analysis>

For evaluation using a guinea pig model system of transplacental infection, guinea pig cytomegalovirus (GPCMV) that exhibits infectivity to guinea pig was used. Since recombinant GPCMV gB proteins may contain aggregates, modified GPCMV gB proteins that are improved in characteristics and do not contain aggregates were prepared.

A gene encoding gB (SEQ ID NO: 15) in which a leader sequence was added to an ectodomain (1-656 aa) in gB derived from the GPCMV strain 22122 and an amino acid mutation for improvement of characteristics was introduced, was artificially synthesized and cloned into pCAGGS1-dhft-neo (Patent Literature 3). It was designed so that a His-tag was added to the C terminus of gB. For expression, Expi293 expression system (Life Technology Inc.) was used. The expression plasmid was transfected into cells and culture supernatant was collected in 4 to 6 days. The culture supernatant containing GPCMV gB was purified using Ni NTA Agarose (QIAGEN) and dialyzed against PBS+0.5 M Arginine to obtain a purified product of the ectodomain of the modified GPCMV gB protein (hereinafter, referred to as "GPCMV-gB").

Figure 2:
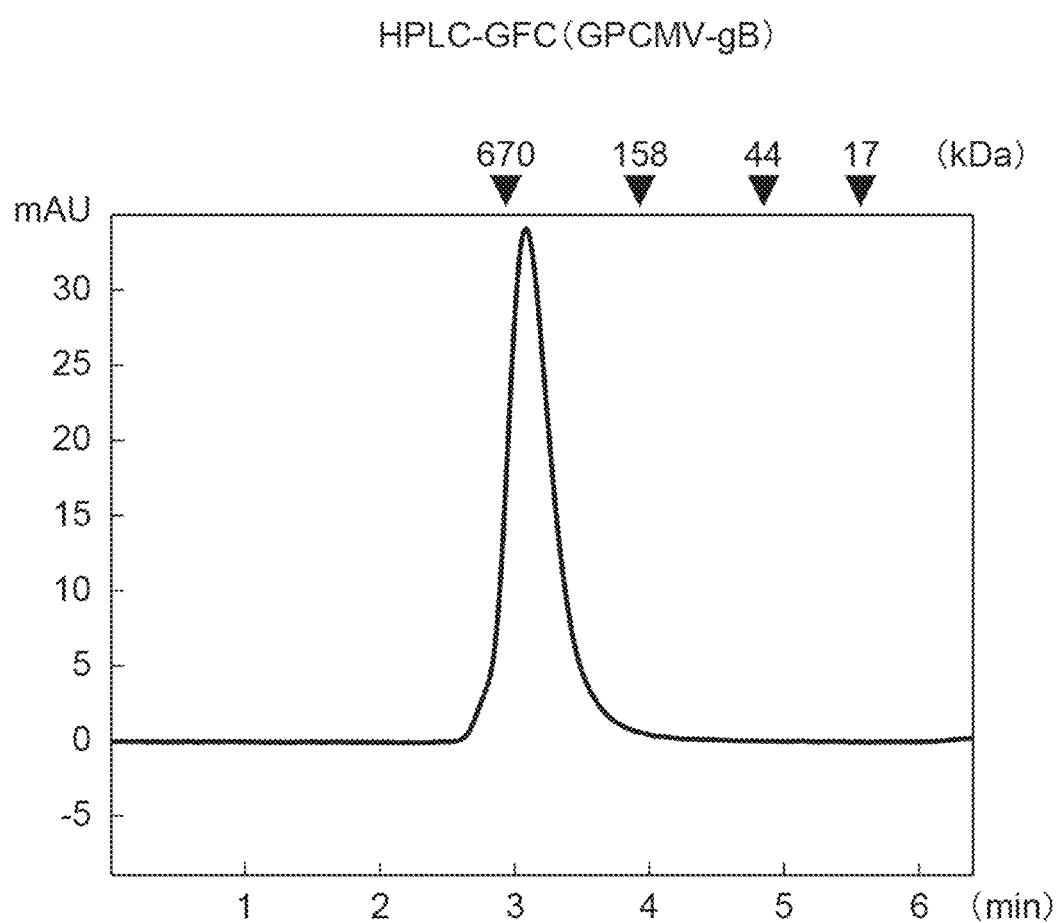
FIG. 2 illustrates a result of characteristic analysis of GPCMV-gB by HPLC gel filtration analysis.

For the purified product of GPCMV-gB, characteristic analysis was conducted as follows. A sample (DTT (+)) subjected to reduction processing with dithiothreitol (DTT) and a sample (DTT (−)) not subjected to the reduction processing were each run by SDS-PAGE in an 8-16% gradient gel and stained with Bullet CBB Stain One (nacalai tesque, INC.). The result is shown in FIG. 1. The lanes 1 and 2 in FIG. 1 are respectively a marker (Bench Mark Prestained Invitogen 10748-010) and 2 µg/lane of purified GPCMV-gB and a band of GPCMV-gB was found as a main band in lane 2. Moreover, as a result of performing HPLC gel filtration analysis at a flow rate of 0.4 mL/min using Superdex 200 Increase 5/150 GL (GE Healthcare) and using PBS as a mobile phase, an expected trimeric peak was found as an almost single peak (FIG. 2).

<Preparation of GPCMV-Pentamer and Characteristic Analysis>

Next, an ectodomain of a pentamer derived from GPCMV strain 22122 was prepared. Since there was no reported case about soluble expression of an ectodomain of a GPCMV pentamer, designing was done as following in reference to a reported case (Non-Patent Literature 14) of soluble expression of an ectodomain of an HCMV pentamer to construct an expression plasmid.

A gene encoding an ectodomain (1-698 aa, SEQ ID NO: 16) of GP75 was artificially synthesized and cloned into pCAGGS1-dhfr-neo. It was designed so that a His-tag was added to the C terminus of GP75. Furthermore, a gene encoding GP115 (1-258 aa, SEQ ID NO: 11) which is an ortholog of HCMV gL, a gene encoding GP129 (1-179 aa, SEQ ID NO: 12) which is an ortholog of HCMV UL128, a gene encoding GP131 (1-192 aa, SEQ ID NO: 13) which is an ortholog of HCMV UL130, and a gene encoding GP133 (1-127 aa, SEQ ID NO: 14) which is an ortholog of HCMV UL131 were each artificially synthesized and cloned into pCAGGS1-dhfr-neo. Expression and purification were performed in a way similar to those of GPCMV-gB and a purified product of the ectodomain (hereinafter, referred to as "GPCMV-Pentamer") of the GPCMV pentamer was obtained.

Figure 3:
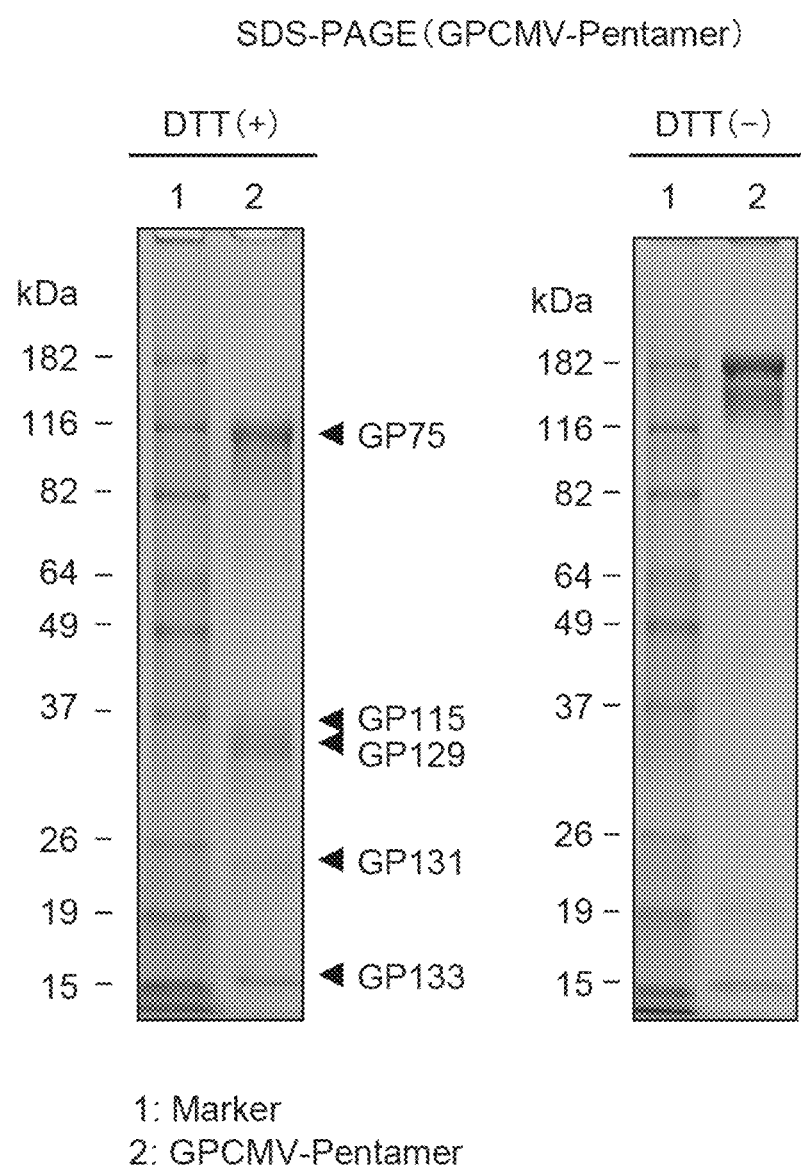
FIG. 3 illustrates a result of characteristic analysis of GPCMV-Pentamer by SDS-PAGE.
Figure 4:
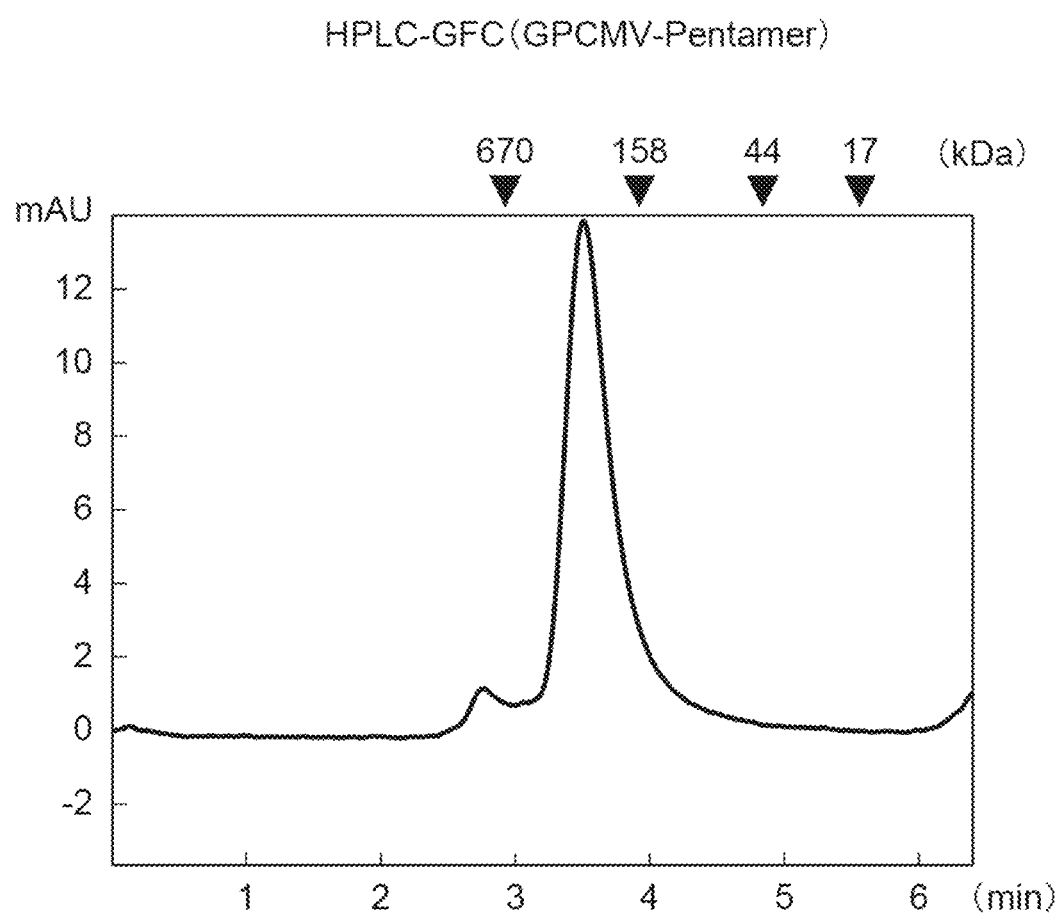
FIG. 4 illustrates a result of characteristic analysis of GPCMV-Pentamer by HPLC gel filtration analysis.

By conducting a characteristic analysis in a way similar to that of GPCMV-gB, bands of various components composing the GPCMV-Pentamer were each found in SDS-PAGE (FIG. 3). Moreover, in an HPLC gel filtration analysis, an expected pentameric (pentamer) peak was found as a main peak (FIG. 4).

<GPCMV/Guinea Pig Immunogenicity Test>

Using prepared GPCMV-gB and GPCMV-Pentamer, a guinea pig immunogenicity test was conducted. For female Hartley guinea pigs in 4 weeks of age, each antigen (GPCMV-gB, GPCMV-Pentamer, or GPCMV-gB+ GPCMV-Pentamer) was prepared to 25 µg/animal with physiological saline (Otsuka Pharmaceutical Co., Ltd.) and 10 v/v % Alum (Invivogen) and 50 µg/animal of CpG ODN1826 (Invivogen) were used as adjuvant. The prepared antigen solutions were inoculated intramuscularly (100 µL/hind limbs and both legs) into Hartley guinea pigs (female 3 animals/group) three times at 2-week intervals and whole blood was collected by cardiac puncture under isoflurane inhalation anesthesia 2 weeks after the final immunization. The obtained bloods were separated into sera in separation tubes containing a setting accelerator and subjected to an inactivation treatment at 56° C. for 30 minutes to prepare immune sera, and a neutralizing antibody inducing ability analysis (neutralizing antibody titer analysis) and a binding antibody inducing ability analysis (binding antibody titer analysis) were conducted using these immune sera.

<Guinea Pig Cells and GPCMV for Neutralizing Antibody Titer Analysis>

For culturing of virus and a neutralizing antibody titer analysis in the fibroblast cell line, GPL cells (CCL 158) purchased from ATCC were used. The medium for cell culturing was prepared by adding 10% FBS (Hyclone), 100 Units/mL Penicillin, 100 µg/mL Streptomycin (Gibco, Cat. No. 15140-122) to F12 (×1) Nutrient Mixture (+) L-glutamine medium (Gibco, Cat. No. 11765-054) and used for expansion, maintenance, and analysis of cells and culturing was performed under conditions at 37° C. and 5% $CO_2$ concentration for them all.

The preparation of macrophages derived from guinea pigs to use for a neutralizing antibody titer analysis was conducted as follows. Splenocytes were harvested and centrifuged to collect cells and suspended in 10-20 mL of 1×RBC (obtained by dissolving 8.26 g of $NH_4Cl$, 1.19 g of $NaHCO_3$, 0.378 g of $EDTA.Na_2$ in 100 mL of sterile water, adjusting pH to 7.3, storing in refrigeration after filtration sterilization, and diluting by 10 times in sterile water at time of use) to lyse erythrocytes. After centrifugation, suspending cells in 1×PBS and then centrifuging were repeated several times and the obtained cells were stored as monocytes at −80° C. after the addition of a medium containing 10% DMSO and 50% FBS, or differentiated into macrophages as they are and used. Guinea pig-derived macrophages to use for a neutralizing antibody titer analysis were cultured at $1.5\text{-}2.5\times10^5$ monocytes/well/96-well plate in the presence of 100 nM TPA for 2 days and, after the removal of supernatant, cells attached to the plate were used as macrophages.

The virus to use for a neutralizing antibody titer analysis was prepared through the following procedure. First, the region 2642-4247 and the region 13030-14482 in the nucleotide sequence of the GPCMV genome (Non-Patent Literature 15) obtained by PCR amplification using DNA extracted from infected cells of the GPCMV strain 22122 (VR-682) purchased from ATCC as a mold were cloned into pBluescript II KS (+). Next, 8.6 kb F plasmid replicon (BAC) and a GFP expression cassette were cloned between 3992 and 3993 of the GPCMV nucleotide sequence in this plasmid. The obtained plasmid was gene-transferred into GPL cells with genomic DNA of the GPCMV strain 22122 and, after five times of subculture of the emerged GFP-expressing virus, cyclic DNA was collected from the infected cells by the Hirt method and gene-transferred by electroporation into *Escherichia coli* DH10B to obtain pBAC-GPCMVA9K. By gene-transferring this BAC DNA into GPL cells, cloned GPCMV-BACA9K that expresses GFP was created (Non-Patent Literature 16).

A purified virus bank for neutralizing antibody titer analyses was prepared as follows. To GPL cells brought to a density of around 70-80%, 1/10 amounts of GPCMV-BACA9K infected GPL cells were added and, after several days of culturing until 60-70% of cells were detached by cytopathic effect, the culture liquid was collected and centrifugation at 1700×g at room temperature was conducted for 10 minutes, the supernatant was collected and slowly overlaid so as not to mix with a sucrose layer in a 30 mL centrifuge tube for ultracentrifugation in which 5 mL of PBS containing 20% sucrose was added first and ultracentrifuged at 70,000×g for 2 hours (rotor: Hitachi Koki P32ST). After removing the supernatant and suspending the pellet into PBS in a ⅕₀ to ¹⁄₁₀₀ volume of the overlaid supernatant, the suspension was dispensed and stored at −80° C. as a purified virus bank for neutralizing antibody titer analyses and each dispensed aliquot was all used up at time of use.

The virus titer of the purified virus bank for neutralizing antibody titer analyses was determined as follows. After thawing a dispensed aliquot of the purified virus stored at −80° C. and preparing a serial dilution with PBS, a 24 well plate was seeded therewith and GPL cells brought to 80-90% were infected therewith and cultured for 1-2 days. Under a fluorescence inverted microscope, GPCMV foci expressing GFP were counted. It was confirmed beforehand that this titer determination method based on the GFP expression and immunostaining method using a monoclonal antibody to GPCMV had the same result.

<GPCMV/Fibroblast Cell Neutralizing Antibody Titer Analysis>

The neutralizing antibody titer analysis using GPL cells was conducted using the activity of reducing the number of foci (focus reduction activity). For the analysis, plates obtained by culturing overnight GPL cells seeded onto 96 well plates (Corning 3596) at 2×10$^4$ cells/well were used. Each immune serum (anti-GPCMV-gB serum, anti-GPCMV-Pentamer serum, or GPCMV-gB+GPCMV-Pentamer serum) was prepared to predetermined concentrations by serial dilution with a medium and mixtures made to 50 µL by adding about 135 PFU of the strain GPCMV-BACA9K thereto were reacted at 37° C. for 30 minutes. A reaction solution in which a medium instead of serum was added was similarly reacted as a negative control. After the inoculation of cells in the analytic plate with 20 µL/well, culturing at 37° C. for 2 hours was conducted to cause adsorption to the cells. The reaction solution was removed and a medium was added and culturing for two days was conducted. The number of GFP-expressing foci was counted using a fluorescence microscope and, based on the result with the reaction solution containing no antibody, the neutralizing antibody titer was determined from the suppression rate of the proportion of the number of cells with each immune serum. The result is shown in Table 1.

<GPCMV/Macrophage Neutralizing Antibody Titer Analysis Test>

The neutralizing antibody titer analysis using macrophages was conducted using infected cell count-reducing activity. For the analysis, macrophages differentiated from monocytes in a 96 well plate (Corning 3596) in the method described above were used. Each immune serum was prepared to predetermined concentrations by serial dilution with a medium and mixtures made to 50 µL by adding about 1350 PFU of the strain GPCMV-BACA9K thereto were reacted at 37° C. for 30 minutes. A reaction solution in which a medium instead of serum was added was similarly reacted as a negative control. After the inoculation of cells in the analytic plate with 20 µL/well, culturing at 37° C. for 2 hours was conducted to cause adsorption to the macrophages. The reaction solution was removed and a medium was added and culturing for 2 days was conducted. GFP-expressing macrophages were counted using a fluorescence microscope and, based on the result with the reaction solution containing no antibody, the neutralizing ability was determined from the suppression rate of the proportion of the number of cells with each immune serum. The result is shown in Table 1.

TABLE 1

| | Serum dilution ratio necessary for 50% suppression | | |
|---|---|---|---|
| Antigen | GPCMV-gB | GPCMV-Pentamer | GPCMV-gB + GPCMV-Pentamer |
| Neutralizing antibody titer (fibroblast cell line) | 40 | 160 | 160 |
| Neutralizing antibody titer (macrophage line) | 640 | >2560 | >2560 |

<GPCMV/Binding Antibody Titer Analysis>

GPCMV-gB or GPCMV-Pentamer was diluted to 1 µg/mL with PBS (Wako) and 50 µL was transferred into a MaxiSorp plate (Nunc) and incubated overnight at 4° C. to perform immobilization. After the immobilization, the plate was washed with PBS and 100 µL each of diluents of each immune serum (anti-GPCMV-gB serum, anti-GPCMV-Pentamer serum, or GPCMV-gB+GPCMV-Pentamer serum) was added to a well in the plate, which was incubated at room temperature. One hour later, the plate was washed with PBST and 100 µL of the detection antibody goat anti-Guinea Pig IgG HRP secondary antibody (Rockland Immunochemicals, Inc. Cat. 606-103-129) was added to the well in the plate, which was incubated at room temperature. One hour later, the plate was washed with PBST, and color development was performed by adding 100 µL of TMB (SIGMA Cat. T-4444) to the well in the plate. 30 minutes later, the reaction was stopped with 1 N sulfuric acid and the optical density value (O.D. 450 nm/650 nm) was measured with a microplate reader (Molecular Devices, LLC). The results of measurement are shown in FIG. 9 and FIG. 10. The GPCMV-gB+GPCMV-Pentamer immune serum exhibited high binding antibody titers to both GPCMV-gB and GPCMV-Pentamer. Based on these, it is considered that immune responses to both of these two kinds of antigens were induced in the GPCMV-gB+GPCMV-Pentamer immunization group.

<Guinea Pig Transplacental Infection Test>

The protective ability of various antigens against transplacental infection in guinea pig was examined in the following way. First, unpregnant female guinea pigs (Hartley, 4 weeks of age) were immunized with the obtained GPCMV-gB and GPCMV-Pentamer described above.

As the group composition, the four-group composition (40 animals per group) of the GPCMV-gB group, the GPCMV-Pentamer group, the GPCMV-gB+GPCMV-Pentamer combined application group, and the physiological saline group as a control group was adopted. 25 µg/animal of each antigen and Alum+CpG as adjuvant were used. A total three times of intramuscular administration were performed at 2-week intervals, antisera were collected two weeks after the third administration, and antisera from 40 animals per group were pooled. Purification of antibody fractions by Protein A column chromatography from the pooled antiserum was conducted. Those dialyzed against PBS after the elution were obtained as antibody fractions.

<Quantification of Guinea Pig IgG>

In order to determine the doses of the antibody fractions, the IgG concentrations in the various guinea pig antisera were quantified by IgG quantitative ELISA.

The IgG quantitative ELISA was conducted through the following procedure. Anti-GUINEA PIG IgG (H & L) (GOAT) Antibody (Rockland Immunochemicals, Inc. Cat. 606-1102) was diluted to 1 µg/mL with PBS (Wako) and 100 µL was transferred into a MaxiSorp plate (Nunc) and incubated overnight at 4° C. to perform immobilization. After the immobilization, the plate was washed with PBS and 100 μL each of the diluents of the various antisera was added to a well in the plate and incubated at room temperature. One hour later, the plate was washed with PBST and 100 μL of an HRP labelled anti-guinea pig IgG antibody (inhouse preparation) was added to the well in the plate, which was incubated at room temperature. One hour later, the plate was washed with PBST, and color development was performed by adding 100 μL of TMB (SIGMA Cat. T-4444) to the well in the plate. 30 minutes later, the reaction was stopped with 1 N sulfuric acid and the optical density value (O.D. 450 nm/650 nm) was measured with a microplate reader (Molecular Devices, LLC). The IgG concentrations in the antisera were quantified by using an anti-HSV gD antibody (inhouse preparation) as a standard preparation and making a standard curve.

As a result, the IgG concentrations in the antisera were 2.71 mg/mL for the GPCMV-gB group, 2.94 mg/mL for the GPCMV-Pentamer group, 3.44 mg/mL for the GPCMV-gB+ GPCMV-Pentamer combined application group, and 1.56 mg/mL for the control group.

Since the serum IgG concentration was 1.6-3.4 mg/mL, an IgG purified product of 15-30 mg/mL was prepared by performing protein concentration using Amicon Ultra (Merck & Co. UFC903024) to administer IgG for one animal in one administration, in the assumption of administration at 2 mL/animal.

IgG purified products were administered to pregnant guinea pigs, which were infected with GPCMV the next day (four animals per group). One week after the infection, antibody fractions were additionally administered.

2 mL each of IgG purified products was intraperitoneally administered to Hartley guinea pigs (pregnant 4 weeks of age). The next day, the wild type GPCMV was subcutaneously inoculated at $1\times10^6$ PFU/individual. For the purpose of making up for metabolized antibodies, 1 mL each of IgG purified products was additionally administered intraperitoneally one week later. After euthanization 3 weeks after the infection, autopsy was conducted to collect the mother's organs (spleen, liver, kidney, lung, salivary gland, placenta) and fetus's organs (liver, lung, brain). After slicing the organs, virus DNA was purified from homogenized specimens using Maxwell 16 Tissue DNA Purification Kit (Promega Corporation) and the virus copy number was calculated by quantitative PCR. The specimens in which the virus copy number of 1 copy or more per $5\times10^5$ cells were detected were determined as "infected". The quantitative PCR was conducted under conditions set forth in Table 2. The primers and probes used are set forth in Table 3.

TABLE 2

Quantitative PCR conditions

| GPCMV GP83 gene detection | μL/ specimen | Guinea pig β actin gene detection | μL/ specimen |
|---|---|---|---|
| Nuclease-free water | 6.69 | Nuclease-free water | 6.24 |
| 2 × master mix[#] | 12.50 | 2 × master mix[#] | 12.50 |
| 100 μg/mL salmon sperm carrier DNA | 0.50 | 100 μg/mL E. coli carrier DNA | 0.50 |
| GP83 primer mix [25 μM] | 0.20 | GP/β actin primer mix [25 μM] | 0.20 |
| GP83 FAM probe [57.9 μM] | 0.11 | GP/β actin FAM probe [11.1 μM] | 0.56 |
| DNA standard preparation | 5.0 | DNA standard preparation | 5.0 |
| Total | 25.0 | Total | 25.0 |

[#]2 × master mix: TaqMan Universal PCR (Applied) or Brilliant II QPCR (Agilent) Master Mix
Cycle conditions: 50° C. for 2 minutes, 95° C. for 10 minutes, [95° C. for 30 seconds, 60° C. for 1 minute] × 50

TABLE 3

Primers and probes

| | For detection of GPCMV GP83 | For detection of guinea pig β actin |
|---|---|---|
| Forward primer | 5'-CGACGACGACGA TGACGAAAAC-3' (SEQ ID NO: 17) | 5'-TGGATCGGCGGC TCATC-3' (SEQ ID NO: 20) |
| Reverse primer | 5'-TCCTCGGTCTCA ACGAAGGGTC-3' (SEQ ID NO: 18) | 5'-CATCGTACTCCT GCTTGCTGAT-3' (SEQ ID NO: 21) |
| FAM probe | 5'-FAM-ATCCGAGT TAGGCAGCG-MGB-3' (SEQ ID NO: 19) | 5'-FAM-CACTCTCC ACCTTCC-MGB-3' (SEQ ID NO: 22) |

Result and Discussion

The results are shown in Table 4. The numerical values in the parentheses represent the number of virus-positive specimens to the number of evaluated specimens (mothers and fetuses are in the number of animals and placentas are in the number of organs). From Table 4, the suppressive effect of congenital infection on fetuses was highest in the gB+Pentamer group. The pentamer group was the second highest and hardly any effect was found in the gB group. Since infection to fetuses was most strongly suppressed in the gB+Pentamer combined application group, it is expected that a new direction of "subunit vaccines containing gB and pentamer together" is effective as an approach toward practical application of CMV vaccines.

TABLE 4

Comparison of infection rate (presence or absence of infection)

| Group | Mother | Placenta | Fetus |
|---|---|---|---|
| GPCMV-gB | 100% (4/4) | 100% (15/15) | 80% (12/15) |
| GPCMV-Pentamer | 75% (3/4) | 50% (7/14) | 43% (6/14) |
| GPCMV-gB + GPCMV-Pentamer | 100% (4/4) | 57% (8/14) | 21% (3/14) |
| Physiological saline | 100% (4/4) | 100% (12/12) | 83% (10/12) |

From the foregoing, infection to fetuses was significantly suppressed, although hardly any effect was exhibited on the first infection in mother guinea pigs in the gB+Pentamer combined application group. The suppressive effect was high compared to those of the respective gB and Pentamer single administration groups. This result is an example that has indicated using an animal pathological model, for the first time, that transmission of virus from mother to fetus can be suppressed more effectively by the coexistence of an anti-gB antibody and an anti-Pentamer antibody and strongly suggests a possibility that a combined application therapy of gB+Pentamer is also effective for suppression of human congenital infection.

[Application to Humans/Preparation of Vaccine Antigen for Humans]

In Examples described above, it has been proved that the administration of the combined application antigens to guinea pig is effective in prevention of transplacental infection and it has been suggested that the combined application antigen is effective as a candidate CMV vaccine for humans. Therefore, HCMV gB and pentamer antigens were prepared for application to humans.

<Preparation of HCMV-gB and Characteristic Analysis>

The modified HCMV-gB protein "gB1-682-fm3Mv9" (hereinafter, referred to as "HCMV-gB") in which amino acid mutations for improvement of characteristics were introduced on the basis of an ectodomain of HCMV-gB derived from the strain AD169 was prepared (SEQ ID NO: 1) and expression and purification were performed in a way similar to those of GPCMV-gB.

Figure 5:
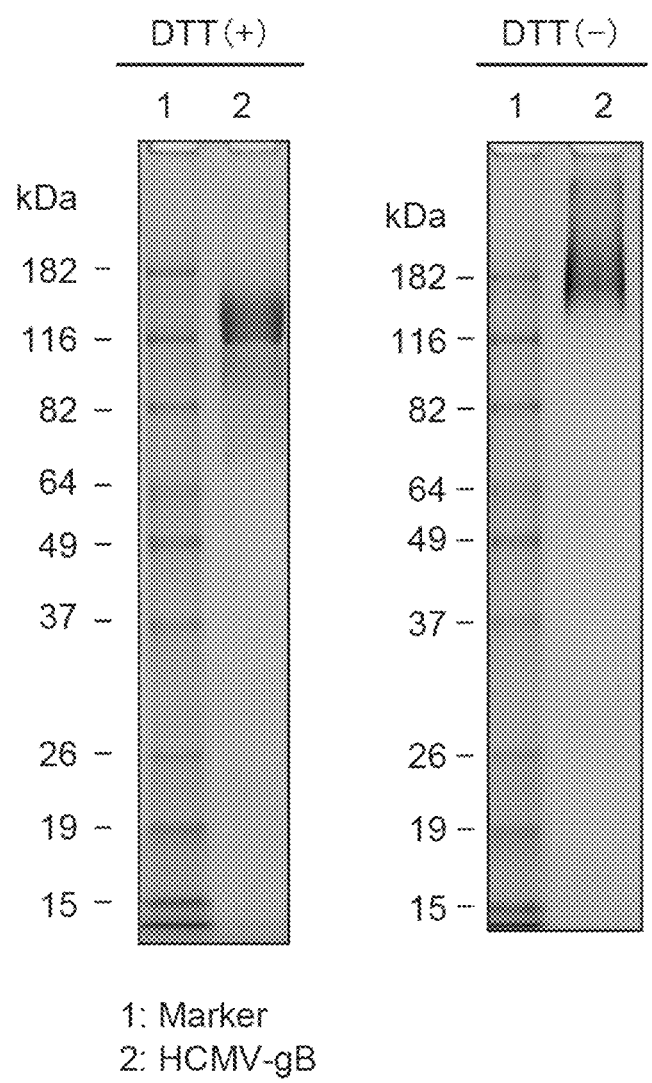
FIG. 5 illustrates a result of characteristic analysis of HCMV-gB by SDS-PAGE.
Figure 6:
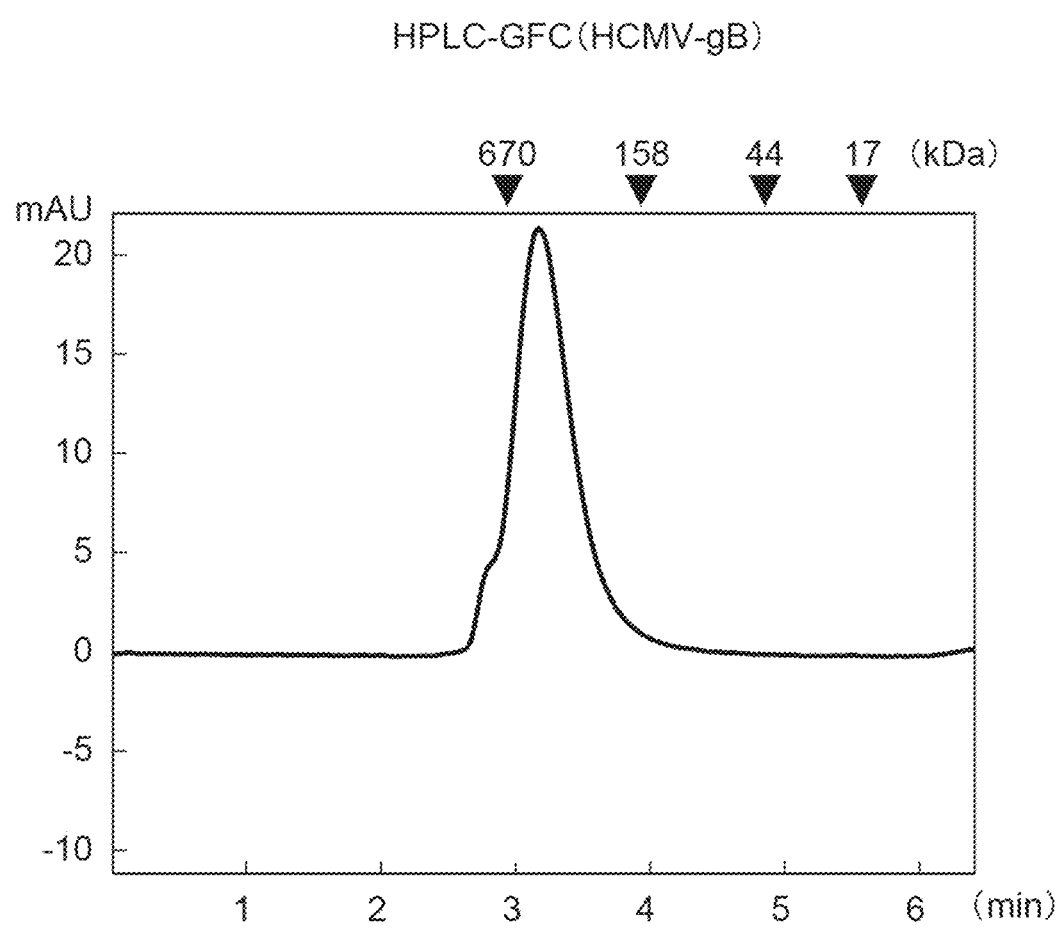
FIG. 6 illustrates a result of characteristic analysis of HCMV-gB by HPLC gel filtration analysis.

The characteristic analysis was also conducted similarly to GPCMV-gB. In SDS-PAGE, a band of HCMV-gB was found as a main band (FIG. 5). Moreover, in an HPLC gel filtration analysis, an expected trimeric peak was found as a main peak (FIG. 6).

<Preparation of HCMV-Pentamer and Characteristic Analysis>

Next, an ectodomain of an HCMV pentamer derived from the strain Merlin was prepared. As proteins composing ectodomains of an HCMV pentamer, UL128 (SEQ ID NO: 4), UL130 (SEQ ID NO: 5), UL131 (SEQ ID NO: 6), gL (SEQ ID NO: 3), and gH (SEQ ID NO: 9) derived from the strain Merlin were used.

Using artificial gene synthesis and genetic engineering techniques, genetic sequences of respective proteins composing the ectodomains of the HCMV pentamer were each cloned into pCAGGS1.dhft.neo vector and a wild type UL128 expression plasmid, a wild type UL130 expression plasmid, a wild type UL131 expression plasmid, a wild type gL expression plasmid, and a wild type gH expression plasmid were prepared. Next, a wild type gH expression plasmid was modified to prepare a secreted type CMV pentamer. In reference to Non Patent Literature 14, a modification that deletes the amino acids from the position 716 and after in the C terminus of gH and adds an LGG linker and a His-tag to the position was made.

Expression and purification were performed in a way similar to those of GPCMV-gB and a purified product of the ectodomain (hereinafter, referred to as "HCMV-Pentamer") of the HCMV pentamer was obtained.

Figure 7:
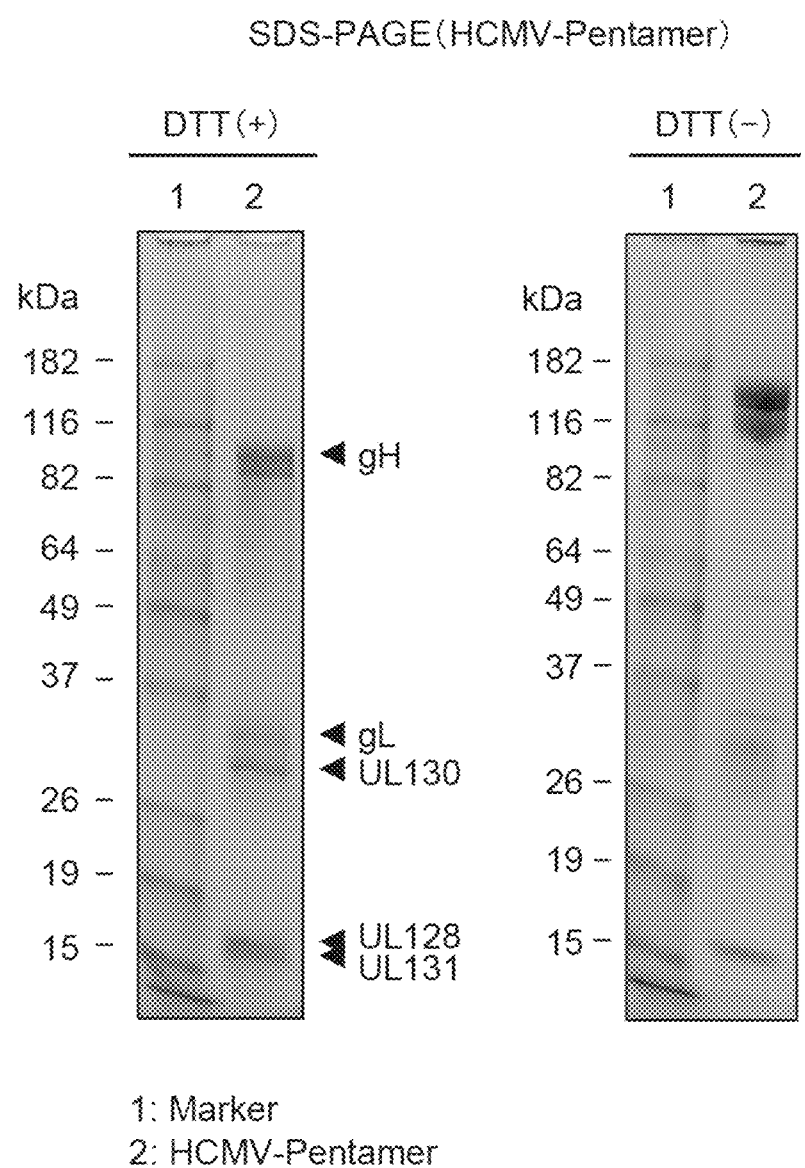
FIG. 7 illustrates a result of characteristic analysis of HCMV-Pentamer by SDS-PAGE.
Figure 8:
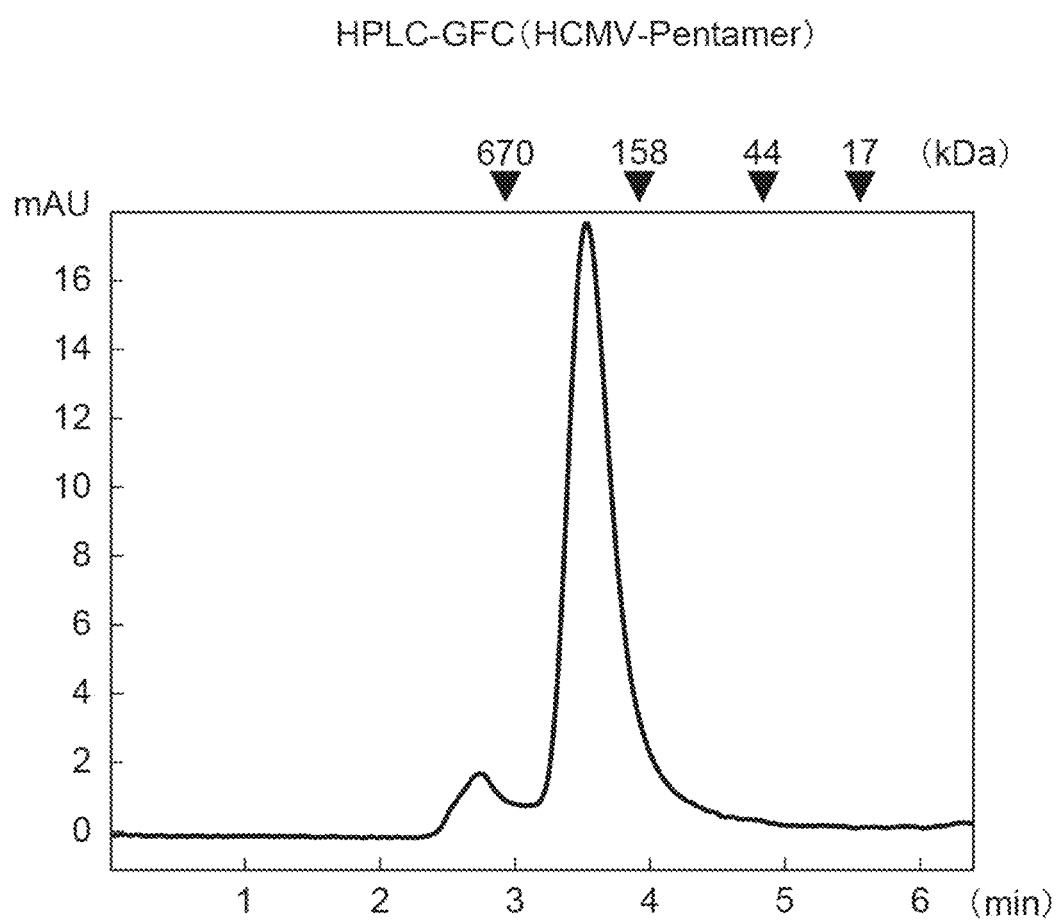
FIG. 8 illustrates a result of characteristic analysis of HCMV-Pentamer by HPLC gel filtration analysis.

When a characteristic analysis was conducted similarly to GPCMV-gB, bands of various components composing the HCMV-Pentamer were each found in SDS-PAGE (FIG. 7). Moreover, in an HPLC gel filtration analysis, an expected pentameric (pentamer) peak was found as a main peak (FIG. 8).

<HCMV/Guinea Pig Immunogenicity Test>

Using prepared HCMV-gB and HCMV-Pentamer, a guinea pig immunogenicity test was conducted. For female Hartley guinea pigs in 4 weeks of age, each antigen (anti-HCMV-gB serum, anti-HCMV-Pentamer serum, or HCMV-gB+HCMV-Pentamer serum) was prepared at 25 μg/animal with physiological saline (Otsuka Pharmaceutical Co., Ltd.) and 10 v/v % Alum (InvivoGen) and 50 μg/animal of CpG ODN1826 (Eurofins) were used as adjuvant. The prepared antigen solutions were inoculated intramuscularly (100 μL/both hind limbs) into Hartley guinea pigs (female 3 animals/group) three times at 2-week intervals and whole blood was collected by cardiac puncture under isoflurane inhalation anesthesia 2 weeks after the final immunization. The obtained bloods were separated into sera in separation tubes containing a setting accelerator and subjected to an inactivation treatment at 56° C. for 30 minutes to prepare immune sera and a binding antibody inducing ability analysis (binding antibody titer analysis) was conducted using these immune sera.

<HCMV/Binding Antibody Titer Analysis>

HCMV-gB or HCMV-Pentamer was diluted to 1 μg/mL with PBS (Wako) and 50 μL was transferred into a MaxiSorp plate (Nunc) and incubated overnight at 4° C. to perform immobilization. After the immobilization, the plate was washed with PBS and 100 μL each of diluents of each immune serum (anti-HCMV-gB serum, anti-HCMV-Pentamer serum, or HCMV-gB+HCMV-Pentamer serum) was added to a well in the plate, which was incubated at room temperature. One hour later, the plate was washed with PBST and 100 μL of the detection antibody goat anti-Guinea Pig IgG HRP secondary antibody (Rockland Immunochemicals, Inc. Cat. 606-103-129) was added to the well in the plate, which was incubated at room temperature. One hour later, the plate was washed with PBST, and color development was performed by adding 100 μL of TMB (SIGMA Cat. T-4444) to the well in the plate. 30 minutes later, the reaction was stopped with 1 N sulfuric acid and the optical density value (O.D. 450 nm/650 nm) was measured with a microplate reader (Molecular Devices, LLC). The results of measurement are shown in FIG. 11 and FIG. 12. The HCMV-gB+HCMV-Pentamer immune serum exhibited high binding antibody titers to both HCMV-gB and HCMV-Pentamer. Based on these, it is considered that immune responses to both of these two kinds of antigens were induced in the HCMV-gB+HCMV-Pentamer immunization group.

<Evaluation of IFN γ Inducing Ability to PBMC of HCMV-Infected Person>

For evaluation of cell-mediated immunity, PBMCs (CTL Cat. CTL-CP1) were used. As PBMCs, specimens derived from 21 donors whose history of having HCMV infection was confirmed with data from CTL were used.

CTL Anti-Aggregate Wash (20×) (CTL Cat. CTL-AA-001) was warmed in a water bath set at 37° C. for ten minutes and completely thawed and 1 mL of CTL Anti-Aggregate Wash (20×) was added to 19 mL of RPMI1640 medium (gibco Cat. 21870-076) to prepare CTL Anti-Aggregate Wash (1×). The prepared CTL Anti-Aggregate Wash (1×) was left to stand for 20 minutes or more under conditions at 37° C. and 5% $CO_2$ until use, and used within one hour. To CTL-Test Medium (CTL Cat. CTLT-010), 1% (v/v) of L-Glutamine (100×) (Wako Cat. 073-05391) was added and was left to stand for 20 minutes or more under conditions at 37° C. and 5% $CO_2$ until use.

A vial containing PBMCs was warmed up in a water bath set at 37° C. for 8 minutes and then the vial was mixed by two times of inversion to suspend PBMCs. All of the cell solution in a vial was transferred to a 50 mL tube and 1 mL of CTL Anti-Aggregate Wash (1×) was transferred into the vial to collect the cell solution completely. While gently swirling the 50 mL tube, 3 mL of CTL Anti-Aggregate Wash (1×) was added over 15 seconds and 5 mL of CTL Anti-Aggregate Wash (1×) was gently further added to prepare a cell solution. The cell solution was centrifuged (330×g, 10 minutes, room temperature) with a setting of rapid acceleration and rapid deceleration, the supernatant was removed after the centrifugation, and cells were suspended by tapping. 10 mL of CTL Anti-Aggregate Wash (1×) was added and were mixed by two times of inversion. The cell solution was centrifuged (330×g, 10 minutes, room temperature) with a setting of rapid acceleration and rapid deceleration, the supernatant was removed after the centrifugation, and cells were suspended by tapping. The cells were diluted to a concentration in a range of $3 \times 10^6$ cells/mL to $5 \times 10^6$ cells/mL with 1×L-Glutamine-CTL-Test Medium.

After a plate accompanying Human IFN-γ ELISpot$^{PLUS}$ (MABTECH AB Cat. 3420-4HST-2) was washed four times with 300 μL/well of D-PBS (−) (Wako Cat. 045-29795), 300 μL/well of 1×L-Glutamine-CTL-Test Medium was added and was left to stand at room temperature for 30 minutes or more. CTL-Test Medium was removed from the plate and 100 μL/well of the cell suspension solution was added. Furthermore, 100 μL/well each of the mixture of HCMV-gB, HCMV-Pentamer, HCMV-gB antigens and the HCMV-Pentamer antigen, a positive control (mAB CD3-2) accompanying Human IFN-γ ELISpot$^{PLUS}$ diluted with 1×L-Glutamine-CTL-Test Medium, and 1×L-Glutamine-CTL-Test Medium as a negative control were added and suspended. The plate was covered with aluminum foil and cultured for 12-24 hours under conditions at 37° C. and 5% $CO_2$.

Figure 13:
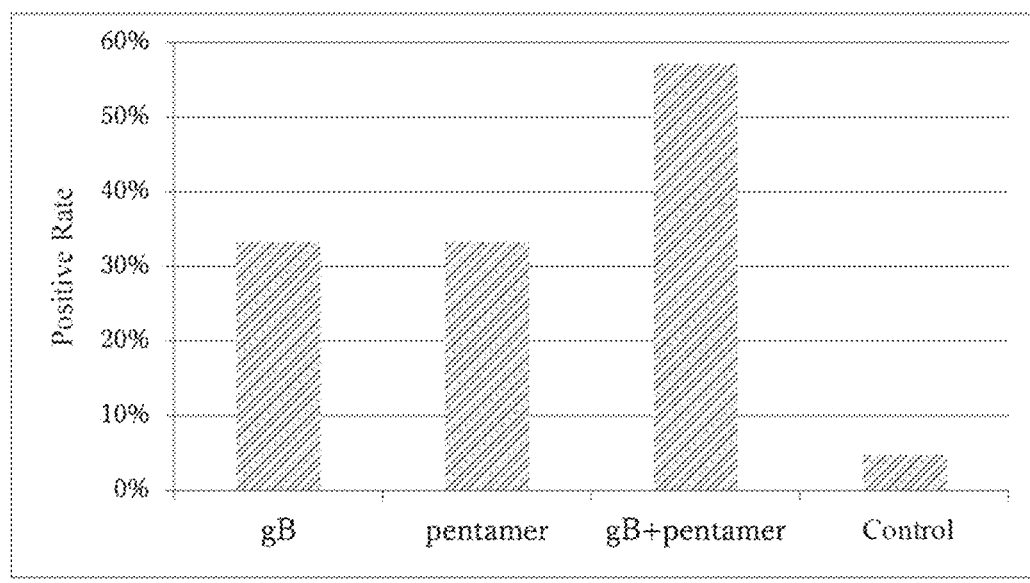
FIG. 13 illustrates the proportion of IFN γ-producing donors when using HCMV-infected patient's PBMCs and giving stimulation with HCMV-gB or HCMV-Pentamer or two of HCMV-gB and HCMV-Pentamer.

A detection antibody (7-B6-1-biotin) accompanying Human IFN-γ ELISpot$^{PLUS}$ was diluted to 1 μg/mL with 0.5% FBS (CORNING Incorporated Cat. 35-076-CV)-PBS to prepare a detection antibody solution. The cells were removed with a medium from the plate and washed 5 times with 300 μL/well of D-PBS (−). 100 μLI well of the detection antibody solution was added and was left to stand at room temperature for 2 hours. Streptavidin-HRP accompanying Human IFN-γ ELISpot$^{PLUS}$ was diluted by 1000 times with 0.5% FBS-PBS to prepare a Streptavidin-HRP solution. After removing the detection antibody solution from the plate and washing 5 times with 300 μL/well of D-PBS (−), 100 μL/well of the Streptavidin-HRP solution was added and was left to stand for one hour at room temperature. Ready-to-use TMB accompanying Human IFN-γ ELISpot$^{PLUS}$ was filtered through a 0.22 μm filter to prepare a Ready-to-use TMB solution. The Streptavidin-HRP solution was removed from the plate and washed 5 times with 300 μL/well of D-PBS (−). After 100 μL/well of the Ready-to-use TMB solution was added to the plate and was left to stand at room temperature within a range of 5-30 minutes until a clear spot was observed, the plate was washed 3 times with 300 μL/well of pure water. Strip wells were removed from the plate frame and the PVDF membrane side of the plate base was rinsed with pure water and the strip wells were dried overnight. Imaging was performed with a CTL ELISPOT reader and the number of spots was counted with a CTL ImmunoSpot S5 verse Analyzer. The specimens in which the spot number of 5 times or more in comparison with the mean spot number value in the negative control (control) well of all specimens was seen were determined "positive for IFNγ induced reaction by antigen stimulation". The ELISpot-positive rate (the proportion of the donors "positive for IFNγ induced reaction by antigen stimulation" to all donors) obtained from the result of determination is shown in FIG. 13.

Result and Discussion

The IFNγ induction was found in more donors when stimulated with a mixture of HCMV-gB and HCMV-Pentamer in comparison with those when stimulated with HCMV-gB or HCMV-Pentamer. Based on these, it is considered that there is a population that cannot induce IFNγ to either antigen of HCMV-gB and HCMV-Pentamer among people infected with HCMV and that cell-mediated immunity can be induced, by administering HCMV-gB and HCMV-Pentamer together as vaccine, not only to the population having cell-mediated immunity inducing ability to any of both antigens, but also to the population that can induce cell-mediated immunity only to either one of the antigens.

The invention claimed is:

1. A method of preventing or treating congenital infection with HCMV in a subject, comprising administering a vaccine which comprises a modified human cytomegalovirus (HCMV) envelope glycoprotein B (gB protein) antigen and a pentamer antigen consisting of HCMV gH, gL, UL128, UL130, and UL131 to the subject, wherein the gB protein antigen is an HCMV gB protein ectodomain variant comprising the amino acid substitutions at positions 156, 157, 239, 240, 456, and 458 in the amino acid sequence set forth in SEQ ID NO:7.

2. The method according to claim 1, wherein the modified gB protein antigen comprises the amino acid sequence set forth in SEQ ID NO: 1.

3. The method according to claim 1, wherein the pentamer antigen is ectodomains of human cytomegalovirus (HCMV) pentamer proteins having the amino acid sequences set forth in SEQ ID NO: 2, SEQ ID NO: 3, SEQ ID NO: 4, SEQ ID NO: 5, and SEQ ID NO: 6.

4. The method according to claim 3, wherein the modified gB protein antigen comprises the amino acid sequence set forth in SEQ ID NO: 1.

* * * * *